United States Patent [19]
Bestwick et al.

[11] Patent Number: 6,054,635
[45] Date of Patent: Apr. 25, 2000

[54] RASPBERRY PROMOTER AND METHODS FOR EXPRESSION OF TRANSGENES IN PLANTS

[75] Inventors: Richard K. Bestwick; Jill A. Kellogg; Helena V. Mathews, all of Portland, Oreg.

[73] Assignee: Agritope, Inc., Portland, Oreg.

[21] Appl. No.: 08/777,147

[22] Filed: Dec. 27, 1996

Related U.S. Application Data

[63] Continuation-in-part of application No. 08/331,355, Oct. 27, 1994, which is a continuation-in-part of application No. 08/261,677, Jun. 17, 1994, Pat. No. 5,750,864.

[51] Int. Cl.$^7$ .............................. C12N 15/29; C12N 5/04; C12N 15/82; A01H 5/00
[52] U.S. Cl. .................. 800/278; 536/24.1; 536/23.1; 800/287; 800/317.4; 435/70.1; 435/468; 435/469; 435/440; 435/410; 435/418; 435/419
[58] Field of Search .................................. 536/24.1, 23.1; 800/287, 317.4, 278; 435/70.1, 468, 469, 440, 410, 418, 419

[56] References Cited

U.S. PATENT DOCUMENTS 5,416,250   5/1995   Ferro, et al. .

FOREIGN PATENT DOCUMENTS

WO91/09112   6/1991   WIPO .
WO94/24294   10/1994   WIPO .

OTHER PUBLICATIONS

Kim et al. Plant Molecular Biology. 1994. vol. 24: 105–117.
Napoli et al. The Plant Cell. 1989. vol. 2: 278–289.
Bestwick, R. K., et al., "Decreased Ethylene Synthesis and Altered Fruit Ripening in Transgenic Tomatoes Expressing S–Adenosylmethionine Hydrolase," HortScience 29:474, abstract No. 306 (1994).
Bestwick, R. K., et al., "Reduced Ethylene Synthesis and Suspended Fruit Ripening in Transgenic Tomatoes Expressing S–Adenosylmethionine Hydrolase," *J. Cell Biochem. Suppl.* 0(16 part a):98 abstract No. X1–208 (1994).

Deikman, J., et al. "Organization of Ripening and Ethylene Regulatory Regions in a Fruit–Specific Promoter from Tomato (*Lycopersicon esculentum*)" *Plant Physiol.* 100:2013–2017 (1992).

Langhoff, D., et al., "Effect of S–Adenosylmethionine Hydrolase Expression on Ethylene Biosynthesis in Transgenic Tomatoes," *J. Chem. Biochem.* 0 (16 part F), abstract No. Y307 (1992).

Lincoln, J. E., et al., "Regulation of Gene Expression by Ethylene During *Lycopersicon esculentum* (Tomato) Fruit Development," *Proc. Natl. Acad. Sci. U.S.A.* 84:2793–2797 (1987).

Lincoln, J. E., and Fischer, R. L., "Regulation of Gene Expression by Ethylene in Wild–Type and vin Tomato (*Lycopersicon essculentum*)Fruit," *Plant Physiol.* 88:370–374 (1988).

Lincoln, J. E., and Fischer,R. L. "Diverse Mechanisms for the Regulation of Ethylene–Inducible Gene Expression." *Mol. Gen. Genet.* 212:71–75 (1988).

Mathews, H., et al. "Genetic Transformation of Red Raspberry with a Gene to Control Ethylene Biosynthesis," *Hort-Science* 29:445, abstract No. 180 (1994).

Montgomery, J., et al., "Identification of an Ethylene–Responsive Region in the Promoter of a Fruit–Ripening Gene," *Proc. Natl. Acad. Sci. U.S.A.* 90:5939–5943 (1993).

*Primary Examiner*—Lynette R. F. Smith
*Assistant Examiner*—Ousama Zaghmout
*Attorney, Agent, or Firm*—Susan T. Evans; Linda R. Judge; Dehlinger & Associates

[57] ABSTRACT

The present invention is directed to the identification and isolation of a promoter region from a raspberry genome. The promoter is operably linked, in a native raspberry genome, to the coding region of a raspberry E4 gene. The raspberry E4 gene promoter of the invention is capable of regulating moderate level, constitutive expression of a heterologous plant gene under its control. The invention is further directed to chimeric genes, cassette vectors, kits, transgenic plants, and methods employing a raspberry E4 promoter.

21 Claims, 10 Drawing Sheets

```
Sequence Range: 1 to 2715
         10         20         30         40         50         60         70
    *     *    *     *    *     *    *     *    *     *    *     *    *     *
AAGCTTAATT GAGATGATTA GCCCAGACCC AGCAGGATTA GGCTTAATGG TGGTCCATTT GAGAAAAAGA 80         90        100        110        120        130        140
    *     *    *     *    *     *    *     *    *     *    *     *    *     *
TTAAAAATGA TGTCATAAAA AAACGTGGTC GGCAGGATTC GAACCTGCGC GGGCAAAGCC ACATGATTTC 150        160        170        180        190        200        210
    *     *    *     *    *     *    *     *    *     *    *     *    *     *
TAGTCATGCC CGATAACCAC TCCGGCACGA CCACAATGAT GCTACAATTG CTTTGTTGTA ATCATTAACT 220        230        240        250        260        270        280
    *     *    *     *    *     *    *     *    *     *    *     *    *     *
TATGGTTGAG TTTGATGCTG ATTAATACTA TTATGTTTCC ATTAACTACT TTGAAGTAT ACAAAATTAC 290        300        310        320        330        340        350
    *     *    *     *    *     *    *     *    *     *    *     *    *     *
GAATTTATAA CCAAATTTGA GGTATAATAT GCGAGAGCTA CCTAAATTTT TCTTACTTAA TTTTAAAGTA 360        370        380        390        400        410        420
    *     *    *     *    *     *    *     *    *     *    *     *    *     *
CATTCAAATT CTGAATTTAT ATTGTGTATA GTCAGAAAAC AATCTACATA TTTAAACACA TAAATTTCTC 430        440        450        460        470        480        490
    *     *    *     *    *     *    *     *    *     *    *     *    *     *
ACGTTTATAA TCAATTTTGT CGGTTCCTGT AATTTTTCTA AAATAAAAAG CAACCAAAAT TGTGCATCAA 500        510        520        530        540        550        560
    *     *    *     *    *     *    *     *    *     *    *     *    *     *
CTTATTACAT ACCATGGGAA ATGCAAACTT CAAAACTTAT GGACTCAAAG GGTACATATC TAAACTACAT 570        580        590        600        610        620        630
    *     *    *     *    *     *    *     *    *     *    *     *    *     *
ATTGTCAGAT TCTTCACTCT TATTTCTTGA GGGCCTCGAG GCATTACCAA CCAAATCCAA AAATTGCTTT 640        650        660        670        680        690        700
    *     *    *     *    *     *    *     *    *     *    *     *    *     *
CGAATCTCAA TAAAAAGGAT AACCCCATGA AAAAGACGTG GACGGCAGGA TTCGAACCTG CGCGCAGAGC 710        720        730        740        750        760        770
    *     *    *     *    *     *    *     *    *     *    *     *    *     *
CCACATGATT TCTAGTCATG CCCGATAACC ACTCCGGCAC GTCCACTTCA CTGTTAACGT TTACAGTAAC 780        790        800        810        820        830        840
    *     *    *     *    *     *    *     *    *     *    *     *    *     *
AAGTCACTAA CTACTAATCA ACATTAGCTC AGGAAATCAA AACTAGATTA TTTACATTTA CAACGACATG >TATA_site
                                                                   |
        850        860        870        880        890        900 |      910
    *     *    *     *    *     *    *     *    *     *    *     * *     *
TCGTTCGAAG TAGTTGGTCT GTATCTGAGT AGCTTTGGCG GGTAGATTCA ATCGCATTTC TGCATATAAA
```

Fig. 1A

```
                >Predicted_transcriptional_start_site
     |
     920      | 930       940       950       960       970
  *    *    *|    *    *    *    *    *    *    *    *    *
ACTGATCCTC CCTCTATCGC CAAAGTCAAA CTGAAA ATG GCT TCC ACC ACC ACC AAC AAC CCA
                                        Met Ala Ser Thr Thr Thr Asn Asn Pro>
                                    ___a___a__RASP E4 EXON1____a___a___>

980       990      1000      1010      1020      1030
  *    *    *    *    *    *    *    *    *    *    *    *
GCT CTA GAC CCA GAT TCG GAC ACT CCG GAT AAT CCG GGT CAC GAG TTT GCT CAA TTC
Ala Leu Asp Pro Asp Ser Asp Thr Pro Asp Asn Pro Gly His Glu Phe Ala Gln Phe>
___a___a___a___a___a___a___a_RASP E4 EXON1____a___a___a___a___a___a___a___>

1040      1050      1060      1070      1080
  *    *    *    *    *    *    *    *    *    *    *
GGA TCC GGG TGC TTC TGG GGA GCC GAG CTC AGG TTT CAG CGA GTG GCC GGT GTG GTC
Gly Ser Gly Cys Phe Trp Gly Ala Glu Leu Arg Phe Gln Arg Val Ala Gly Val Val>
___a___a___a___a___a___a___a_RASP E4 EXON1____a___a___a___a___a___a___a___>

1090      1100      1110      1120      1130      1140
  *    *    *    *    *    *    *    *    *    *    *
AAG ACC GAG GTT GGG TAC TCC CAG GGC CAC GTC CAC GAT CCG AAT TAC AAA CTG GTC
Lys Thr Glu Val Gly Tyr Ser Gln Gly His Val His Asp Pro Asn Tyr Lys Leu Val>
___a___a___a___a___a___a___a_RASP E4 EXON1____a___a___a___a___a___a___a___>

1150      1160      1170      1180      1190      1200
  *    *    *    *    *    *    *    *    *    *    *    *
TGC TCC GGA ACT ACC AAC CAT TCG GAG GTC GTT CGG GTC CAG TTC GAC CCG CAA GTC
Cys Ser Gly Thr Thr Asn His Ser Glu Val Val Arg Val Gln Phe Asp Pro Gln Val>
___a___a___a___a___a___a___a_RASP E4 EXON1____a___a___a___a___a___a___a___>

1210      1220      1230      1240      1250
  *    *    *    *    *    *    *    *    *    *    *
TAC CCA TAC TCG GAC CTG CTT TCC GTC TTT TGG TCT CGT CAT GAT CCA ACG ACT GTC
Tyr Pro Tyr Ser Asp Leu Leu Ser Val Phe Trp Ser Arg His Asp Pro Thr Thr Val>
___a___a___a___a___a___a___a_RASP E4 EXON1____a___a___a___a___a___a___a___>

>5'_splice_site
   |
1260     |1270      1280      1290      1300      1310      1320
  *    * |  *    *    *    *    *    *    *    *    *    *    *
AAT CGC CAG GTA TGGGGATTGG GGACTTCTGT TTTCATTTGA ATTTTGATGC TAAAAAATTT
Asn Arg Gln>
___a___a___>
___b_____b_____b_____INTRON_____b_____b_____>

1330      1340      1350      1360      1370      1380      1390
  *    *    *    *    *    *    *    *    *    *    *    *    *    *
CTTGCTTTTT CATACTACAC AGTACACACA AAAAGTTGTG TTTTTTTTTC ATTCTTTTAA ATAGTAGTTG
_____b_____b_____b_INTRON___b_____b_____b_____>
```

Fig. 1B

```
             1400        1410        1420        1430        1440        1450        1460
              *     *     *     *     *     *     *     *     *     *     *     *     *     *
        GAAAAGTGCT CTTGGAGTTG AAGAGTACTT CAGTATTGCA TATGGTCTCA GTGAAATTGA TAGTGATTAA
        _____b_____b_____b__INTRON____b_____b_____b_____>

1470        1480        1490        1500        1510        1520        1530
         *     *     *     *     *     *     *     *     *     *     *     *     *     *
        TCATAAGGAT GTTTGTGATT AAAGGCAGGA TGCATTTTGT GTATGANTGA TTTTGGGTAG AATATTTTTG
        _____b_____b_____b__INTRON____b_____b_____b_____>

1540        1550        1560        1570        1580        1590        1600
              *     *     *     *     *     *     *     *     *     *     *     *     *     *
        GAACAGTTAA AATTTATGGG CTGCTGCACA CTGGCTATGA ACAAATGTAT AGCATTAAAG TGCTTATGAC
        _____b_____b_____b__INTRON____b_____b_____b_____>

1610        1620        1630        1640        1650        1660        1670
              *     *     *     *     *     *     *     *     *     *     *     *     *     *
        AAATTCACAA TTGTATATTA GCAGCAGAGA CATTAAAGTT TCTAAATGCC TTTTAAGTAG TTGGAAAAAA
        _____b_____b_____b__INTRON____b_____b_____b_____>

1680        1690        1700        1710        1720        1730        1740
              *     *     *     *     *     *     *     *     *     *     *     *     *     *
        GTGCTTTTTT TGGTTGAAGA AGCACATTCA CTATTTGCCT GTTAATGGAA TTGGTAATGA TGAATCACAA
        _____b_____b_____b__INTRON____b_____b_____b_____>

1750        1760        1770        1780        1790        1800        1810
              *     *     *     *     *     *     *     *     *     *     *     *     *     *
        GGATATTTGT GAATACAAGC AGGATGCTTT TAGTGTGCAA GTGATCTTTC GGAACATTTA AAATGTATAA
        _____b_____b_____b__INTRON____b_____b_____b_____>

>3'_splice_site
                                                                         |
             1820        1830        1840        1850        1860        1870        |
              *     *     *     *     *     *     *     *     *     *     *     *   * |
        CAAAGGTGTA ACATAAGAAG GCTTTGAAAT ATTCTCAATT TCTCATTGAT TGAATGAATT ATGTGTTAG
        _____b_____b_____b__INTRON____b_____b_____b_____>

1880        1890        1900        1910        1920
        1930
         *     *     *     *     *     *     *     *     *     *     *     *
        GGT GGA GAT GTG GGT ACT CAA TAT CGA TCT GGA ATA TAC TAC TAC AAC GAA ACG CAG
        Gly Gly Asp Val Gly Thr Gln Tyr Arg Ser Gly Ile Tyr Tyr Tyr Asn Glu Thr Gln>
        ___c___c___c___c___c___c___c__RASP E4 EXON 2____c___c___c___c___c___c___c___>

1940        1950        1960        1970        1980        1990
              *     *     *     *     *     *     *     *     *     *     *     *
        GCC CGT CTA GCA CAG GAA TCA AAG GAA GCA AAG CAA CTG GAG TTT AAG GAT AAG AAG
        Ala Arg Leu Ala Gln Glu Ser Lys Glu Ala Lys Gln Leu Glu Phe Lys Asp Lys Lys>
        ___c___c___c___c___c___c___c__RASP E4 EXON 2____c___c___c___c___c___c___c___>
```

Fig. 1C

```
               2000           2010           2020           2030           2040           2050
         *       *       *       *       *       *       *       *       *       *       *       *
GTG GTG ACA GAG ATT CTT CCA GCA AAG AGG TTT TAC AGG GCA GAG GAG TAC CAT CAG
Val Val Thr Glu Ile Leu Pro Ala Lys Arg Phe Tyr Arg Ala Glu Glu Tyr His Gln>
___c____c____c____c____c____c____c__RASP E4 EXON 2____c____c____c____c____c____c____c___>

2060           2070           2080           2090           2100
         *       *       *       *       *       *       *       *       *       *       *
CAA TAT CTC GCA AAG GGA GGA GGT AAT GGC AAC AAA CAA TCT GCT GAA AAA GGT TGC
Gln Tyr Leu Ala Lys Gly Gly Gly Asn Gly Asn Lys Gln Ser Ala Glu Lys Gly Cys>
___c____c____c____c____c____c____c__RASP E4 EXON 2____c____c____c____c____c____c____c___>

2110           2120           2130           2140           2150           2160           2170
  *       *       *       *       *       *       *       *       *       *       *       *       *
AAT GAT CCT ATT CGA TGC TAT GGT TGA GAAACT AATGCATTAT GCCATTATTA AAACTCTACT
Asn Asp Pro Ile Arg Cys Tyr Gly ***>
___c____c__RASP E4 EXON 2___c____c___>

2180           2190           2200           2210           2220           2230           2240
         *       *       *       *       *       *       *       *       *       *       *       *       *
GGTTTACTAT GCAGAAACAC CTATGTCAGT TCAATTATAC TGAAGGCACC AAAGTGTCAT CTTAAATTAT

>Predicted_poly_A_site
                |
        2250           2260     |     2270           2280           2290           2300           2310
         *       *       *       *    |*       *       *       *       *       *       *       *       *
ATGGCAATGT TTTACTCGTT ATGAATAAAG GAGGTCCAAG TCGACCAGAT ATGAACAAAT GAAATATTGC 2320           2330           2340           2350           2360           2370           2380
         *       *       *       *       *       *       *       *       *       *       *       *       *
CATGTTAATT GGAATCCAGT AGTAATTAGG ATTTGTTTTG GTGTATGTAC TCCGATATCA GATATGCAAA 2390           2400           2410           2420           2430           2440           2450
         *       *       *       *       *       *       *       *       *       *       *       *       *
TGATGCATTG TGTTTTTATA TATTGACAAG TTCCAAATTA TAGTACTTCG TATGTGTTAT GCGGTTTAAT 2460           2470           2480           2490           2500           2510           2520
         *       *       *       *       *       *       *       *       *       *       *       *       *
TAGTGTTGCT TACTTGAATG GTATATTACT ATTATGCTTA GTAGGAACTA GGAACTAGGG AATATGTTGT >Predicted_poly_A_site
                                |
        2530           2540           2550           2560    |    2570           2580           2590
         *       *       *       *       *       *       *       *       *       *       *       *       *
GATAGAGTTG TCCAACGAAA TTTTTGACCA AAGTTATTTC ATTGAATAAA AACTACAGAT CTTAGAGATA 2600           2610           2620           2630           2640           2650           2660
         *       *       *       *       *       *       *       *       *       *       *       *       *
CATCCAATTC TATAAAGTGA AAGAAGCAAA TATTATTTGT TCATGAGGCT ATGAGTCATG AACTTTATGC 2670           2680           2690           2700           2710
         *       *       *       *       *       *       *       *       *
TATAACCGAA GCAACCTCAG AAAAGTCGAA GTAAATTGTG TATTGTTTAG AGCTC
```

Fig. 1D

```
           10         20         30         40         50         60         70
    *      *   *      *   *      *   *      *   *      *   *      *   *      *
AAGCTTAATT GAGATGATTA GCCCAGACCC AGCAGGATTA GGCTTAATGG TGGTCCATTT GAGAAAAAGA 80         90        100        110        120        130        140
    *      *   *      *   *      *   *      *   *      *   *      *   *      *
TTAAAAATGA TGTCATAAAA AAACGTGGTC GGCAGGATTC GAACCTGCGC GGGCAAAGCC ACATGATTTC 150        160        170        180        190        200        210
    *      *   *      *   *      *   *      *   *      *   *      *   *      *
TAGTCATGCC CGATAACCAC TCCGGCACGA CCACAATGAT GCTACAATTG CTTTGTTGTA ATCATTAACT 220        230        240        250        260        270        280
    *      *   *      *   *      *   *      *   *      *   *      *   *      *
TATGGTTGAG TTTGATGCTG ATTAATACTA TTATGTTTCC ATTAACTACT TTTGAAGTAT ACAAAATTAC 290        300        310        320        330        340        350
    *      *   *      *   *      *   *      *   *      *   *      *   *      *
GAATTTATAA CCAAATTTGA GGTATAATAT GCGAGAGCTA CCTAAATTTT TCTTACTTAA TTTTAAAGTA 360        370        380        390        400        410        420
    *      *   *      *   *      *   *      *   *      *   *      *   *      *
CATTCAAATT CTGAATTTAT ATTGTGTATA GTCAGAAAAC AATCTACATA TTTAAACACA TAAATTTCTC 430        440        450        460        470        480        490
    *      *   *      *   *      *   *      *   *      *   *      *   *      *
ACGTTTATAA TCAATTTTGT CGGTTCCTGT AATTTTTCTA AAATAAAAAG CAACCAAAAT TGTGCATCAA 500        510        520        530        540        550        560
    *      *   *      *   *      *   *      *   *      *   *      *   *      *
CTTATTACAT ACCATGGGAA ATGCAAACTT CAAAACTTAT GGACTCAAAG GGTACATATC TAAACTACAT 570        580        590        600        610        620        630
    *      *   *      *   *      *   *      *   *      *   *      *   *      *
ATTGTCAGAT TCTTCACTCT TATTTCTTGA GGGCCTCGAG GCATTACCAA CCAAATCCAA AAATTGCTTT 640        650        660        670        680        690        700
    *      *   *      *   *      *   *      *   *      *   *      *   *      *
CGAATCTCAA TAAAAAGGAT AACCCCATGA AAAAGACGTG GACGGCAGGA TTCGAACCTG CGCGCAGAGC 710        720        730        740        750        760        770
    *      *   *      *   *      *   *      *   *      *   *      *   *      *
CCACATGATT TCTAGTCATG CCCGATAACC ACTCCGGCAC GTCCACTTCA CTGTTAACGT TTACAGTAAC 780        790        800        810        820        830        840
    *      *   *      *   *      *   *      *   *      *   *      *   *      *
AAGTCACTAA CTACTAATCA ACATTAGCTC AGGAAATCAA AACTAGATTA TTTACATTTA CAACGACATG

>TATA_site
                                                                      |
          850        860        870        880        890        900 |     910
    *      *   *      *   *      *   *      *   *      *   *      *  |*      *
TCGTTCGAAG TAGTTGGTCT GTATCTGAGT AGCTTTGGCG GGTAGATTCA ATCGCATTTC TGCATATAAA >Predicted_transcriptional_start_site
       |
      920      | 930        940        950        960        970
    *  |   *   *|  *   *      *   *      *   *      *   *      *
ACTGATCCTC CCTCTATCGC CAAAGTCAAA CTGAAA ATG GCT TCC ACC ACC ACC AAC AAC CCA
                                         Met Ala Ser Thr Thr Thr Asn Asn Pro>
                                   ___a___a__RASP E4 EXON1____a___a___>
```

Fig. 5

RASPBERRY PROMOTER AND METHODS FOR EXPRESSION OF TRANSGENES IN PLANTS

This application is a continuation-in-part of U.S. patent application Ser. No. 08/331,355, filed on Oct. 27, 1994, herein incorporated by reference, which is a continuation-in-part of U.S. application Ser. No. 08/261,677, filed Jun. 17, 1994, now U.S. Pat. No. 5,750,864, also herein incorporated by reference.

FIELD OF THE INVENTION

The present invention relates to the identification of promoters from raspberry which are capable of regulating constitutive expression of heterologous plant genes, and to chimeric genes, cassette vectors, kits, transgenic plants, and methods employing such promoters.

REFERENCES

Adams, D. O., and Yang, S. F., *Plant Physiology* 70:117–123 (1977).

Akama, K. et al., *Plant Cell Reports* 14(7):450–454 (1995).

Ausubel, F. M., et al., in *CURRENT PROTOCOLS IN MOLECULAR BIOLOGY,* John Wiley and Sons, Inc., Media Pa. (1992).

Balazs, E., et al., *Gene* 19(3):239–249 (1982).

Beachy, R., et al., *Annu. Rev. Phytopathol.* 28:451–74 (1990).

Beck, et al., *Gene* 19:327–336 (1982).

Bellini, C., et al., *Bio/Technol* 7(5):503–508 (1989).

Benvenuto, E., et al., XXIst Annual Meeting of the Italian Society for Agricultural Genetics, Como, Italy, Sep. 30–Oct. 2, 1987 *Genet. Agrar.* 42(1) (1988).

Bestwick, R. K., et al., PCT International Publication No. WO 95/35387, published Dec. 28, 1995.

Brunke, K. J. and Wilson, S. L., European Patent Publication No. 0 559 603 A2, published Sep. 8, 1993.

Chang, C., et al., *Science,* 262:539–544 (1993).

Comai, L. and Coning, A. J., U.S. Pat. No. 5,187,267, issued Feb. 16, 1993.

Cordes, S., et al., *Plant Cell* 1:1025–1034 (1989).

Dayhoff, M. O., in *ATLAS OF PROTEIN SEOUENCE AND STRUCTURE* Vol. 5, National Biomedical Research Foundation, pp. 101–110, and Supplement 2 to this volume, pp. 1–10 (1972).

Deikman, J., et al., *EMBO J.* 7:3315 (1988).

Deikman, J., et al., *Plant Physiol.* 100:2013 (1992).

Delanney, X., et al., *Crop Science* 35(5):1461–1467 (1995).

Ferro, A., et al., U.S. Pat. No. 5,416,250, issued May 16, 1995.

Fillatti, J., et al., *Biotechnology* 5:726–730 (1987).

Fraley, R., et al., U.S. Pat. No. 5,352,605, issued on Oct. 4, 1994.

Fry, J., et al., *Plant Cell Reports* 6:321:325 (1987).

Gritz, L., et al., *Gene* 25:179–188 (1983).

Guilley, H., et al., *Cell* 30(3):763–773 (1982).

Hood, E., et al., *J. Bacteriol.* 168:1291–1301 (1986).

Hooykaas, P. J. J., and Schilperoot, R. A., *TRENDS IN BIOCHEMICAL SCIENCES.,* International Union of Biochemistry and Elsevier Science Publishers, v. 10(8):307–309 (Aug. 1985).

Hughes, J. A., et al., *J. Bact.* 169:3625–3632 (1987).

Jefferson, R. A., et al., *EMBO J.* 6:3901 (1987a).

Jefferson, R. A., *Plant Mol. Biol. Rep.* 5:387 (1987b).

Jongedijk, E., et al., *Euphytica* 85:173–180 (1995).

Kawasaki, E. S., et al., in *PCR TECHNOLOGY: PRINCIPLES AND APPLICATIONS OF DNA AMPLIFICATON* (H. A. Erlich, ed.) Stockton Press (1989).

Klein, T. M., et al., *PNAS* (USA) 85(22):8502–8505 (1988).

Lee, J. J., et al., *Meth. of Enzymol.* 152:633–648 (1987).

Leisner, S. M., and Gelvin, S. B., *Proc. Hatl. Acad. Sci. USA* 85(8):2553–2557 (1988).

Maniatis, T., et al., in *MOLECULAR CLONING: A LABORATORY MANUAL,* Cold Spring Harbor Laboratory (1982).

Melchers, L. S., et al., *Plant J.* 5:469–480 (1994).

Miki, B. L. A., et al., *PLANT DNA INFECTIOUS AGENTS* (Hohn, T., et al., Eds.) Springer-Verlag, Wien, Austria, pp.249–265 (1987).

Montgomery, J., et al., *Proc. Natl. Acad. Sci., USA,* 90:5939–5943 (1993).

Mullis, K. B., U.S. Pat. No. 4,683,202, issued Jul. 28, 1987.

Mullis, K. B., et al., U.S. Pat. No. 4,683,195, issued July 28, 1987.

Nagel, R., et al., *FEMS Microbiol. Lett.* 67:325 (1990).

Ni, M., et al., *Plant J.* 7:661–676 (1995).

Odell, J. T., et al., *Nature* 313:810–812 (1985).

Odell, J. T., et al., *J. Cell Biochem.* (Suppl. 11B):60 (1987).

Odell, J. T., et al., *Plant Mol Biol* 10(3):263–272 (1988).

Pearson, W. R., *Methods in Enzymology* 183:63–98 (1990).

Pearson, W. R. and Lipman, D. J., *PNAS* 85:2444–2448 (1988).

Picton, S., et al., *Plant Physiology* 103(4):1471–1472 (1993).

Ponstein, A. S., et al., *Plant Physiology* 104:109–118 (1994).

Reed, A. J., et al., *J. of Agricultural and Food Chemistry* 44:388–394 (1996).

Rogers, S., U.S. Pat. No. 5,034,322, issued on Jul. 23, 1991.

Rogers, S., U.S. Pat. No. 5,378,619, issued on Jan. 3, 1995.

Saiki, R. K., et al., *Science* 239:487–491 (1988).

Sambrook, J., et al., in *MOLECULAR CLONING: A LABORATORY MANUAL,* Cold Spring Harbor Laboratory Press, Vol. 2 (1989).

Schaller, G. E., Bleecker, A. B., *Science* 270:1809–1811 (1995).

Stalker, D., et al., *Science* 242:419–423 (1988).

Tinius, C. N., et al., *Crop Science* 35(5):1451–1461 (1995).

Toubart, P., et al., *Plant J.* 3:367–373 (1992).

Tommerup, H., et al., *Eur. Congr. Biotechnol.* 5:916–918 (1990).

Van Den Elzen, P. L. M., et al, "Virus and Fungal Resistance: From Laboratory to Field" in: *THE PRODUCTION AND USES OF GENETICALLY TRANSFORMED PLANTS* (Bevan, M. W., et al., Eds), Royal Society Discussion Meeting, Chapman and Hall Ltd., London England, 1994.

Veluthambi, K., et al., *J. Bacteriol.* 170(4):1523–1532 (1988).

Wang, A. M., et al. in *PCR PROTOCOLS: A GUIDE TO METHODS AND APPLICATIONS* (M. A. Innis, et al., Eds.) Academic Press (1990).

Woloshuk, C. P., et al., *J. Plant Cell* 3:619–628 (1991).

Yao, J. L., et al., *Plant Cell Reports* 14(7):407–412 (1995).

Zhou, H., et al., *Plant Cell Reports* 15:159–163 (1995).

Zhu, Q., et al., *Plant Cell* 7:1681–1689 (1995).

BACKGROUND OF THE INVENTION

Promoters that regulate gene expression in plants are essential elements of plant genetic engineering. Several examples of promoters useful for the expression of selected genes in plants are now available (Zhu, et al., 1995; Ni, et al., 1995).

To be expressed in a cell, a gene must be operably linked to a promoter which is recognized by certain enzymes in the cell. The 5' non-coding regions of a gene (i.e., regions immediately 5' to the coding region), referred to as promoters or transcriptional regulatory regions, initiate transcription of the gene to produce a mRNA transcript. The mRNA is then translated at the ribosomes of the cell to yield an encoded polypeptide.

Promoters typically contain from about 500–1500 bases, and can provide regulated expression of genes under their control. A promoter used for expressing a heterologous gene in plant cells may be characterized as (i) a constitutive promoter, that is, a promoter capable of causing similar levels of gene expression in all or many plant tissues, or, (ii) a tissue selective promoter, that is, one which is capable of regulating gene expression to select tissues in a plant transformant (e.g., leaves or fruit).

Many such promoters have been characterized, including those derived from plant viruses, Agrobacterium genes, and a variety of plant genes. Considerable effort has gone into the isolation and characterization of constitutive promoters to drive the expression of a variety of heterologous genes in plant systems.

Viral promoters (i.e., promoters from viral genes) for expressing selected genes in plants, have been identified in the caulimovirus family of viruses (a group of double-stranded DNA viruses), and include the Cauliflower Mosaic Virus (CaMV) 35S (Balazs, et al, 1982; Guilley, et al., 1982; Odell, et al., 1985; Odell, et al., 1987; Odell, et al., 1988; Tommerup, et al., 1990; Jefferson, et al., 1987a; Jefferson, 1987b) and CAMV 19S promoters (Fraley, et al., 1994), and the Figwort Mosaic Virus (FMV) (Rogers, 1995) promoter. Promoters useful for regulating gene expression in plants and obtained from bacterial sources, such as Agrobacterium-derived promoters, have been identified and isolated. Such promoters include those derived from Agrobacterium T-DNA opine synthase genes, and include the nopaline synthase (nos) promoter (Rogers, 1991), the octopine synthase (ocs) promoter (Leisner and Gelvin, 1988) and mannopine synthase (mas) promoter.

Plant promoters (promoters derived from plant sources) effective to provide constitutive expression, are less well known, and include hsp80, Heat Shock Protein 80 from cauliflower, (Brunke and Wilson, 1993), and the tomato ubiquitin promoter (Picton, et al., 1993). These promoters can be used to direct the constitutive expression of heterologous nucleic acid sequences in transformed plant tissues. At present, a relatively small number of plant promoters, particularly constitutive plant promoters, has been identified. The use of such promoters in plant genetic engineering has been rather limited to date, since gene expression in plants is, for the most part, typically tissue, developmentally, or environmentally-regulated.

SUMMARY OF THE INVENTION

The present invention is directed to a raspberry promoter which provides moderate-level, constitutive expression of a nucleic acid sequence placed under its control. A promoter of the invention can also confer constitutive expression on heterologous, non-constitutive promoters.

In one aspect, the present invention is directed to a promoter which is operably linked, in a native raspberry genome, to the coding region of a raspberry E4 gene. Chimeric genes of the present invention contain a DNA sequence encoding a product of interest under the transcriptional control of a raspberry E4 promoter. The DNA sequence is typically heterologous to the promoter and is operably linked to the promoter to enable constitutive expression of the product.

In one embodiment, the product is a polypeptide that permits selection of transformed plant cells containing the chimeric gene by rendering such cells resistant to an amount of an antibiotic that would be toxic to non-transformed cells. Exemplary products include, but are not limited to, aminoglycoside phosphotransferases, such as neomycin phosphotransferase and hygromycin phosphotransferase. In one such embodiment, a chimeric gene of the invention contains an hpt gene sequence encoding hygromycin phosphotransferase II under the transcriptional control of a raspberry E4 promoter. In an alternate embodiment, a chimeric gene of the invention contains an nptII gene sequence encoding neomycin phosphotransferase II under the transcriptional control of a raspberry E4 promoter.

In another embodiment, the product is a polypeptide that confers herbicide-resistance to transformed plant cells expressing the polypeptide. In one such embodiment, a chimeric gene of the present invention contains a bxn gene encoding a bromoyxnil-specific nitrilase under the transcriptional control of a raspberry E4 promoter. Transformed plants containing this chimeric gene express a bromoxynil-specific nitrilase and are resistant to the application of bromoxynil-containing herbicides. other exemplary DNA sequences encoding genes conferring herbicide resistance include the EPSP synthase gene (encoding 5-enolpyruvylshikimate-3-phosphate synthase enzyme), which confers resistance to glyphosate; an acetolactate synthase gene, which confers resistance to the herbicide "GLEAN"; a bialaphos resistance gene (the bar gene) coding for phosphinothricin acetyltransferase (PAT), and the glyphosate-tolerant genes, CP4 and GOX. Chimeric genes of the invention contain one or more of these herbicide-resistance genes, operationally linked to a raspberry E4 promoter.

In another embodiment, the DNA sequence or cDNA sequence encodes a viral coat protein, such as alfalfa mosaic virus coat protein, cucumber mosaic virus coat protein, tobacco streak virus coat protein, potato virus coat protein, tobacco rattle virus coat protein, and tobacco mosaic virus coat protein. According to one such embodiment, a chimeric gene of the invention contains a viral coat protein gene, such as ALMV, CMV, TSV, PVX, TRV, or TMV, under the transcriptional control a raspberry E4 promoter.

Alternatively, the DNA sequence corresponds to a gene encoding a dominant defective protein, such as mutant forms of the ETR1 gene, which confers ethylene insensitivity. In yet another embodiment, the DNA sequence corresponds to a gene capable of altering a plant biochemical pathway, such as the ACCD gene. The ACCD gene forms a product which degrades a precursor in the ethylene biosynthetic pathway.

One aspect of the invention includes an isolated DNA molecule comprising a constitutive raspberry promoter, which in a native raspberry genome, is operably linked to the coding region of a raspberry E4 (RE4) gene. An exemplary RE4 promoter sequence is contained in SEQ ID NO:2, and also presented herein as SEQ ID NO:1. The sequence of the RE4 promoter region corresponds to nucleotides 1 through 946 (inclusive) of SEQ ID NO:2 (FIGS. 1A–1D). The sequence of the RE4 promoter is also presented as FIG. 5. Smaller fragments of such a promoter region may be derived from this sequence, where the smaller fragments are effective to regulate constitutive expression of a DNA sequence under their control.

The present invention also includes the use of any of the above chimeric genes, DNA constructs, and isolated DNA sequences to generate a plant transformation vector. Such vectors can be used in any plant cell transformation method, including, Agrobacterium-based methods, electroporation, microinjection, and micro-projectile bombardment. These vectors may also form part of a plant transformation kit. Other components of the kit may include, but are not limited to, reagents useful for plant cell transformation.

In another embodiment, the present invention includes a plant cell, plant tissue, transgenic plant, fruit cell, whole fruit, seeds or calli containing a raspberry E4 promoter, or any of the above-described chimeric genes, vectors or DNA constructs.

In another aspect of the present invention, the promoter described herein is employed in a method for providing moderate expression of a heterologous gene, such as a selectable marker gene, in transgenic plants. In this method, a chimeric gene of the present invention containing a DNA sequence encoding a selectable marker product (e.g., a neomycin phosphotransferase or hygromycin phosphotransferase) is introduced into progenitor cells of a plant. Transgenic plants containing the chimeric gene are selected by their ability to grow in the presence of an amount of selective agent (e.g., hygromycin, geneticin or kanamycin) that is toxic to non-transformed cells. The transformed plant cells thus selected are then regenerated to provide a differentiated plant, followed by selection of a transformed plant which expresses the product.

Further, the invention includes a method for producing a transgenic fruit-bearing plant. In this method a chimeric gene of the present invention, typically carried in an expression vector allowing selection in plant cells, is introduced into progenitor cells of selected plant. These progenitor cells are then grown to produce a transgenic plant.

The method may further comprise isolation of a raspberry E4 promoter by the following steps:

(i) selecting a probe DNA molecule containing a sequence homologous to a region of raspberry E4 gene DNA,
(ii) contacting the probe with a plurality of target DNA molecules derived from a raspberry genome under conditions favoring specific hybridization between the probe molecule and a target molecule homologous to the probe molecule,
(iii) identifying a target molecule having a DNA sequence homologous to the raspberry E4 gene, and
(iv) isolating promoter sequences associated with the target molecule, and
(v) evaluating one or more of the isolated sequences or portion thereof for its ability to regulate constitutive expression of a downstream gene under its control.

The chimeric genes, vectors, constructs, isolated DNA molecules, products and methods of the present invention can be produced using the raspberry E4 promoter sequences essentially as described above.

These and other objects and features of the invention will become more fully apparent when the following detailed description is read in conjunction with the accompanying figures and examples.

BRIEF DESCRIPTION OF THE FIGURES

FIGS. 1A–1D shows a DNA sequence of an isolated E4 gene from a raspberry genomic DNA library;

FIG. 5 presents the DNA sequence of the raspberry E4 promoter, RE4; and

DETAILED DESCRIPTION OF THE DRAWINGS

I. Definitions

Figure 2:
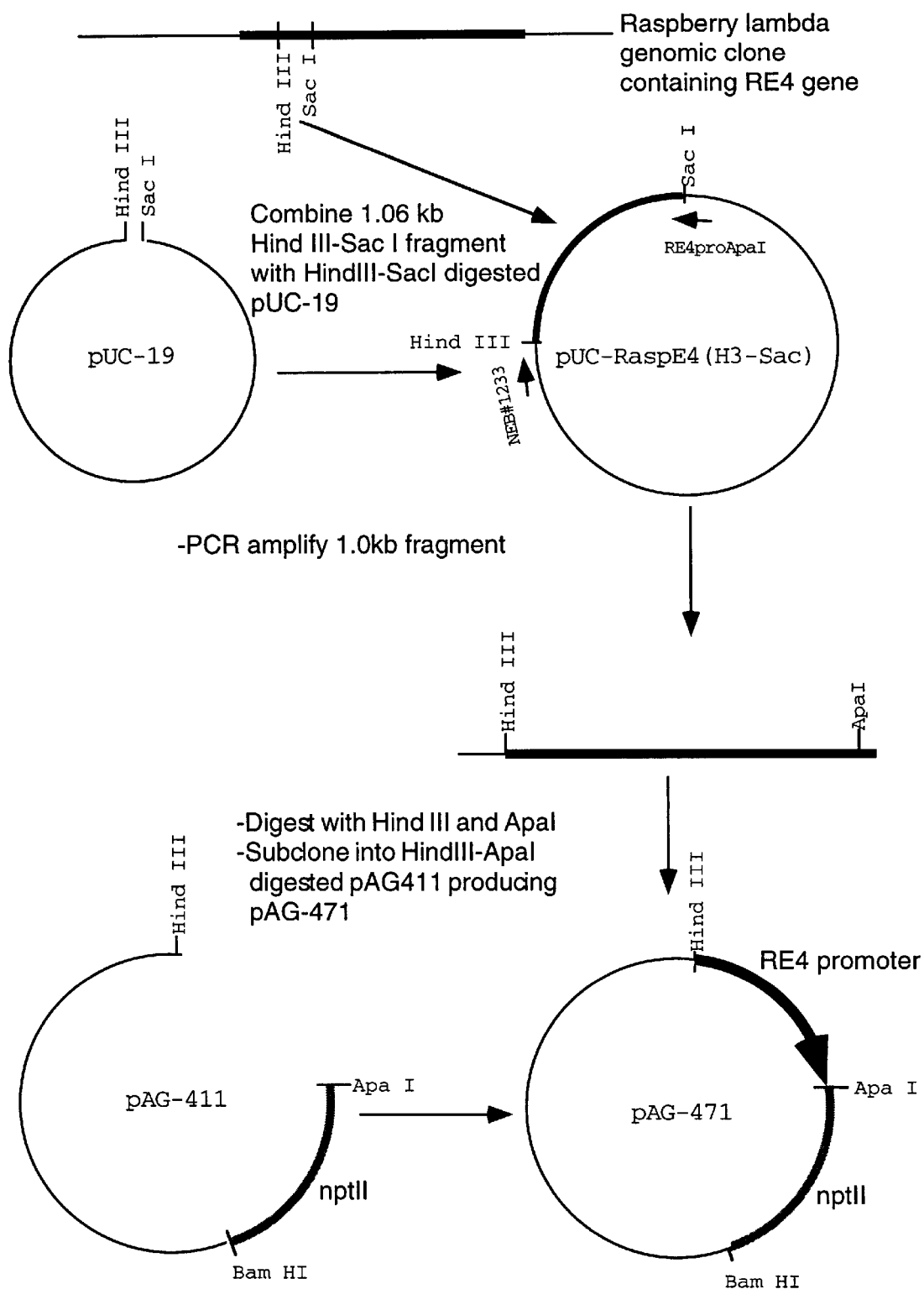
FIG. 2 is a schematic diagram of the steps followed in constructing vector pAG-471 containing a chimeric RE4-nptII gene.

The following terms, as used herein, have the meanings as indicated:

"Chimeric gene" as defined herein refers to a non-naturally occurring gene which is composed of parts of different genes. A chimeric gene is typically composed of a promoter sequence operably linked to a "heterologous" DNA sequence. A typical chimeric gene of the present invention, for transformation into a plant, will include a raspberry promoter (e.g., an RE4 promoter), a heterologous structural DNA coding sequence (e.g., the aminoglycoside phosphotransferase nptII gene) and a 3' non-translated polyadenylation site.

A "constitutive" promoter refers to a promoter that directs RNA production in many or all tissues of a plant transformant, as opposed to a tissue-specific promoter, which directs RNA synthesis at higher levels in particular types of cells and tissues (e.g., fruit specific promoters such as the tomato E4 or E8 promoter (Cordes, et al., 1989; Bestwick, et al., 1995).

By "promoter" is meant a sequence of DNA that directs transcription of a downstream heterologous gene, and includes promoters derived by means of ligation with operator regions, random or controlled mutagenesis, addition or duplication of enhancer sequences, addition or modification with synthetic linkers, and the like.

By "plant promoter" is meant a promoter (as defined above), which in its native form, is derived from plant genomic DNA.

"Raspberry promoter" refers to a promoter (as defined above) which, in its native form, is derived from a raspberry genome. For example, an RE4 promoter is a regulatory promoter region which is operably linked, in a native raspberry genome, to the coding region of a raspberry E4 gene (RE4).

A raspberry promoter derived from a specified gene (e.g., a raspberry promoter derived from the RE4 gene, such as RE4pro) includes a promoter in which at least one or more regions of the promoter are derived from the specified raspberry gene. An exemplary promoter of this type is one in which, e.g., one region of the RE4 promoter is replaced by one or more sequences derived from a different gene, without substantially reducing the expression of the resulting chimeric gene in a host cell, or altering the function of the unaltered RE4 promoter.

"Promoter strength" refers to the level of promoter-regulated (e.g, RE4pro) expression of a heterologous gene in a plant tissue or tissues, relative to a suitable standard (e.g., caulimovirus cassava mottle vein virus promoter CAS or the hsp80 promoter). Expression levels can be measured by linking the promoter to a suitable reporter gene such as GUS (β-glucuronidase), dihydrofolate reductase, or nptII (neomycin phosphotransferase II). Expression of the reporter gene can be easily measured by fluorometric, spectrophotometric or histochemical assays (Jefferson, et al., 1987a; Jefferson, 1987b).

For the purposes of the present invention, a moderate promoter is one that drives expression of a reporter gene at about 10–300% of the level obtained with a promoter such as hsp80.

A "heterologous" DNA coding sequence is a structural coding sequence that is not native to the plant being transformed, or a coding sequence that has been engineered for improved characteristics of its protein product.

Heterologous, with respect to the promoter, refers to a coding sequence that does not exist in nature in the same gene with the promoter to which it is currently attached.

A gene considered to share sequence identity with the raspberry E4 gene, or a particular region or regions thereof, has at least about 60% or preferably 80% global sequence identity over a length of polynucleotide sequence corresponding to the raspberry E4 polynucleotide sequences disclosed herein (e.g., SEQ ID NOs:1 and 2).

"Sequence identity" is determined essentially as follows. Two polynucleotide sequences of the same length (preferably, corresponding to the coding sequences of the gene) are considered to be identical (i.e., homologous) to one another, if, when they are aligned using the ALIGN program, over 60% or preferably 80% of the nucleic acids in the highest scoring alignment are identically aligned using a ktup of 1, the default parameters and the default PAM matrix (Dayhoff, 1972).

The ALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

Two nucleic acid fragments are considered to be "selectively hybridizable" to a polynucleotide derived from a raspberry E4 gene, if they are capable of specifically hybridizing to the coding sequences or a variants thereof or of specifically priming a polymerase chain amplification reaction: (i) under typical hybridization and wash conditions, as described, for example, in Maniatis, et al. (1982), pages 320–328, and 382–389; (ii) using reduced stringency wash conditions that allow at most about 25–30% basepair mismatches, for example: 2×SSC (contains sodium 3.0 M NaCl and 0.3 M sodium citrate, at pH 7.0), 0.1% sodium dodecyl sulfate (SDS) solution, room temperature twice, 30 minutes each; then 2×SSC, 0.1% SDS, 37° C., once, for 30 minutes; then 2×SSC, at room temperature twice, for 10 minutes each, or (iii) selecting primers for use in typical polymerase chain reactions (PCR) under standard conditions (for example, in Saiki, et al., 1988), which result in specific amplification of sequences of the desired target sequence or its variants.

Preferably, highly homologous nucleic acid strands contain less than 20–40% basepair mismatches, even more preferably less than 5–20% basepair mismatches. These degrees of homology (i.e., sequence identity) can be selected by using wash conditions of appropriate stringency for identification of clones from gene libraries (or other sources of genetic material), as is well known in the art.

A "raspberry E4 encoded polypeptide" is defined herein as any polypeptide homologous to a raspberry E4 encoded polypeptide. In one embodiment, a polypeptide is homologous to an RE4 encoded polypeptide if it is encoded by nucleic acid that selectively hybridizes to sequences of the raspberry E4 gene or its variants.

In another embodiment, a polypeptide is homologous to a raspberry E4 encoded polypeptide if it is encoded by raspberry E4 or its variants, as defined above. Polypeptides of this group are typically larger than 15, preferable 25, or more preferable 35, contiguous amino acids. Further, for polypeptides longer than about 60 amino acids, sequence comparisons for the purpose of determining "polypeptide homology" are performed using the local alignment program LALIGN. The polypeptide sequence is compared against the raspberry E4 amino acid sequence or any of its variants, as defined above, using the LALIGN program with a ktup of 1, default parameters and the default PAM.

Any polypeptide with an optimal alignment longer than 60 amino acids and greater than 55% or preferably 80% of identically aligned amino acids is considered to be a "homologous polypeptide." The LALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

A polynucleotide is "derived from" raspberry E4 if it has the same or substantially the same basepair sequence as a region of the RE4 protein coding sequence, cDNA of RE4 or complements thereof, or if it displays homology as noted above.

A polypeptide or polypeptide "fragment" is "derived from" raspberry E4 if it is (i) encoded by a raspberry E4 gene, or (ii) displays homology to RE4 encoded polypeptides as noted above.

In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

As used herein, a "plant cell" refers to any cell derived from a plant, including undifferentiated tissue (e.g., callus) as well as plant seeds, pollen, progagules and embryos.

II. Identification and Isolation of a Raspberry E4 Promoter

The present invention is directed to the applicants' discovery of a promoter from *Rubus idaeus* (red raspberry).

The promoter has been isolated and characterized, and experiments performed in support of the invention demonstrate that the new raspberry promoter functions as moderate-level, constitutive promoter. The isolation and characterization of an exemplary promoter, a promoter isolated from a raspberry E4 gene, referred to herein as RE4pro, is described below.

A. Identification of a Raspberry E4 Promoter

The raspberry E4 promoter was obtained from a raspberry homologue of the tomato E4 gene. The identification of a raspberry E4 gene, and the isolation of a raspberry E4 promoter (RE4pro), will now be described.

The tomato E4 gene, which is present as a single copy in the tomato genome, has been isolated (Cordes, et al., 1989). Although the precise function of the E4 gene is still unknown, the tomato E4 gene is transcriptionally activated at the onset of ripening, coincident with an increase in ethylene biosynthesis (Montgomery, et al., 1993). The tomato E4 promoter is both stage and tissue specific (Cordes, et al., 1989), and typically, E4 mRNA is abundant in ripening tomato fruit and is not detected in leaf, root, stem, or unripe fruit.

To detect the presence of an E4 gene in various plant species such as raspberry, a southern blot experiment is carried out. Southern blot experiments performed in support of the present invention demonstrate the presence of DNA molecules in raspberry having a high degree of sequence identity to the tomato E4 gene. Similar Southern blot analyses may be performed on other plants to identify additional E4 genes, such as those described in Example 1.B (e.g., strawberry, melon, carnation, cauliflower).

A Southern blot analysis is detailed in Example 1B. E4 homologues are identified in a Southern blot of the genomic DNA of a plant of interest, probed with a labelled DNA fragment containing the coding sequence of the tomato E4 gene. The sequence of the tomato E4 gene is presented herein as SEQ ID NO:5.

Preferably, the probe is selected to contain the coding sequence of the tomato E4 gene rather than the promoter sequence, since coding sequences are typically more conserved from species to species than are promoter sequences. This approach is further supported by the finding that the RE4 promoter does not share sequence identity (or promoter function) with the tomato E4 promoter, as will be discussed in greater detail below.

Returning now to the Southern blot experiments detailed in Example 1, probe molecules are generated from tomato genomic DNA using primer-specific amplification (Mullis, 1987; Mullis, et al., 1987). The oligonucleotide primers are selected such that the amplified region includes the entire coding sequence of the tomato E4 gene. Primers may also be selected to amplify only a selected region of the E4 gene.

Alternatively, a probe can be made by isolating restriction-digest fragments containing the sequence of interest from plasmid DNA.

The probe is labeled with a detectable moiety to enable subsequent identification of homologous target molecules. Exemplary labeling moieties include radio-active nucleotides, such as $^{32}$P-labeled nucleotides, digoxygenin-labeled nucleotides, biotinylated nucleotides, and the like, available from commercial sources.

In the case of a primer-amplified probe, labeled nucleotides may be directly incorporated into the probe during the amplification process. Probe molecules derived from DNA that has already been isolated, such as restriction-digest fragments from plasmid DNA, are typically end-labeled (Ausubel, et al., 1992).

Target molecules, such as HindIII DNA fragments from the genomes of the above-listed plants, are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules.

Conditions favoring specific hybridization are referred to as moderately-to-highly stringent, and are affected primarily by the salt concentration and temperature of the wash buffer (Ausubel, et al., 1992; Sambrook, et al., 1989). Hybridization conditions are typically classified as moderately stringent, due to the low salt concentration, and are expected to preserve only specific hybridization interactions, allowing the identification and isolation of homologous genes in different plant species.

Following contacting, hybridization, and washing, target molecules with sequences substantially identical to the probe are identified by detecting the label on the probe. The label may be detected directly, for example, as in a radioactive label detected on auto-radiograms, such as in Example 1.B, or it may be detected with a secondary moiety, for example, fluorescently-labeled streptavidin binding to a biotinylated probe.

B. Isolation of a Raspberry E4 Promoter, RE4pro

Following the identification of plants containing E4 genes, such as raspberry, the DNA encoding the genes, including the 5' regulatory regions, may be isolated from the respective species, by, for example, screening a genomic DNA library. Experiments performed in support of the present invention, detailed in Examples 1.C and 1.D, demonstrate the isolation of a genomic copy of a raspberry E4 gene from a raspberry genomic DNA library.

The library of interest is screened with a probe containing sequences corresponding to the coding sequence of a known E4 gene, such as the tomato E4 gene. The screening is done using known methods (Ausubel, et al., 1992; Sambrook, et al., 1989), essentially as described above.

Positive plaques or colonies are isolated, and the insert DNA is sequenced and compared to known E4 sequences. Clones containing inserts with sequences corresponding to genes homologous to tomato E4 are identified and, if necessary, used to obtain additional clones until the promoter region of interest is identified and further isolated. The sequence of the raspberry E4 gene is presented in FIGS. 1A–D and also as SEQ ID NO:2. The corresponding protein sequence is presented herein as SEQ ID NO:8 and is also shown in FIGS. 1A–D.

The nucleotide sequence corresponding to a 0.95 kb fragment derived from one such RE4-containing lambda clone is presented as SEQ ID NO:1, and represents the raspberry promoter of the invention, a raspberry E4 promoter, designated herein as RE4pro. A DNA fragment containing the RE4 promoter, RE4pro, was isolated by digesting one of the RE4-containing lambda clones with HindIII and SacI, resulting in the release of a 1.06 kb fragment. This fragment was then purified by electrophoresis on agarose gel to provide the full-length transcript promoter of the raspberry E4 gene.

Characterization of the RE4-containing genomic clone allows isolation of the RE4 promoter. The raspberry promoter can then be used to regulate expression of a heterologous gene. An exemplary RE4 promoter has the sequence presented as SEQ ID NO:1.

The construction of a representative subclone containing the RE4 promoter, pAG-471, is presented in FIG. 2 and also described in Example 2.

III. Plant Transformation

In support of the present invention, exemplary chimeric genes containing a raspberry plant promoter sequence operably linked to a heterologous DNA sequence, were constructed. Exemplary chimeric gene constructs include RE4pro::nptII (Example 3B). The protein expressed by the nptII gene, neomycin phosphotransferase, is an aminoglycoside phosphotransferase which confers kanamycin resistance to transgenic plants expressing the product. This protein, as well as other selectable marker products, and products conferring herbicide resistance, may function more efficiently if expressed (i) constitutively, and (ii) at moderate levels (rather than being overexpressed) in transgenic plants. Accordingly, the RE4 promoter represents an ideal promoter for satisfying this objective.

A. Construction of Agrobacterium Binary Plant Transformation Vectors

Figure 3:
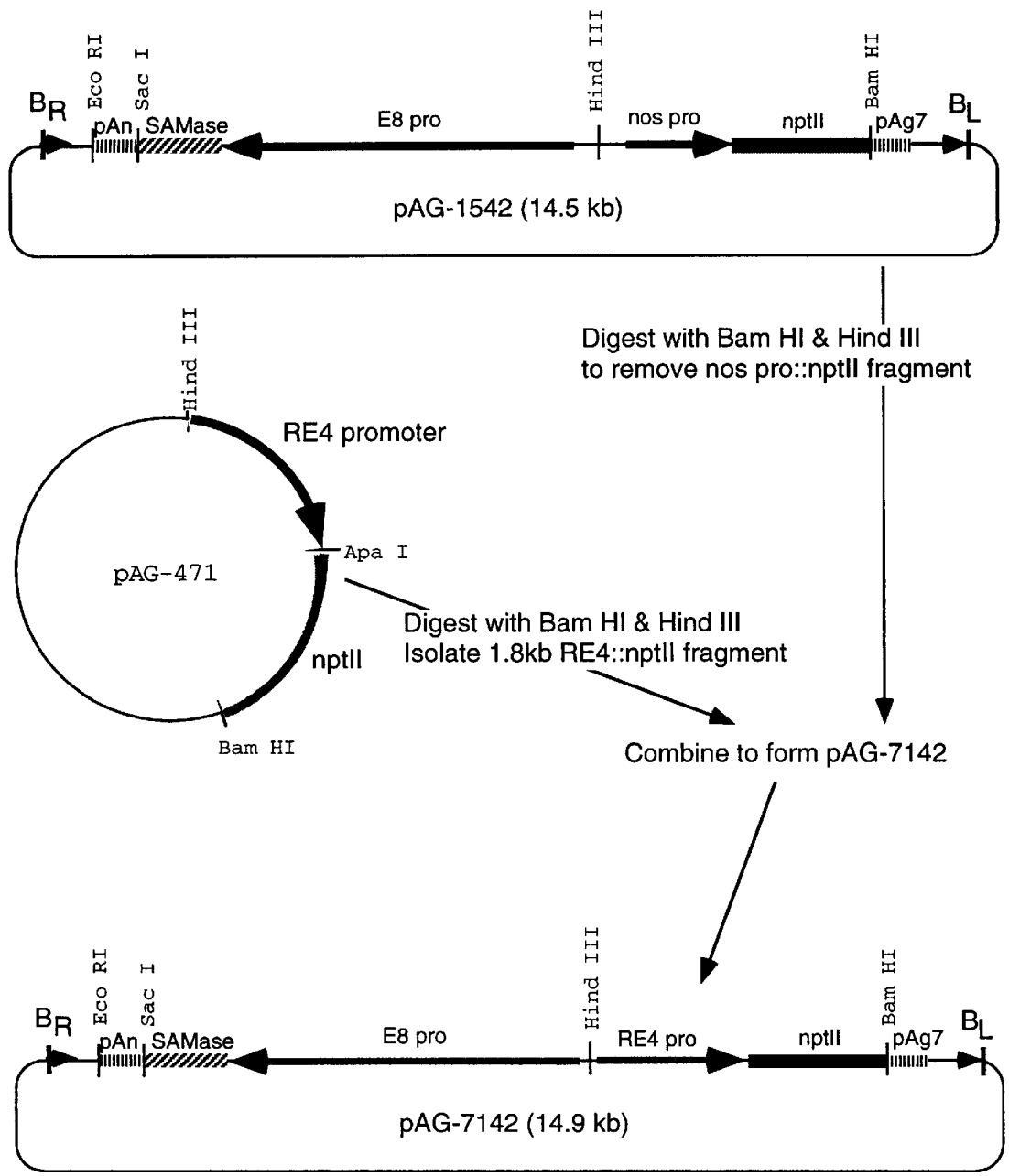
FIG. 3 schematically represents the steps followed in constructing Agrobacterium binary vector, pAG-7142, containing the raspberry RE4 promoter fused to the nptII gene, and illustrates the placement of selected enzyme cleavage sites. The Agrobacterium Ti right and left borders are abbreviated $B_R$ and $B_L$, respectively.

Construction of an exemplary Ayrobacterium binary vector, pAG-7142, containing the chimeric RE4pro:nptII gene described above, can be performed as described in Example 3B, and as schematically represented in FIG. 3. This binary vector also contains a gene encoding SAMase, S-adenosylmethionine hydrolase (Ferro, et al., 1995; Hughes, et al., 1987), which is immaterial to the present invention.

1. Construction of Binary Plant Transformation Vector. pAG-7142

Binary plant transformation vector, pAG-7142, is constructed by inserting a 1.8 kb RE4pro::nptII fragment from plasmid pAG-471 (described in section II.B above), at the BamHI and HindIII sites of plasmid pAG-1542, from which the nos pro::nptII fragment has been excised.

Plasmid pAG-1542 can be prepared using conventional cloning techniques known in the art (Sambrook, et al., 1989). This illustrative subcloning binary vector contains a neomycin phosphotransferase II selectable marker gene (nptII) gene under the control of the nos promoter located near the left border, and the SAMase gene (Ferro, et al., 1995) driven by the tomato E8 promoter (Deikman, et al., 1988; Deikman, et al., 1992) located near the right border. As previously stated, the presence of the tomato E8:SAMase construct is immaterial to the expression results described herein.

FIG. 3 illustrates the construction and structure of *Agrobacterium tumefaciens* binary vector, pAG-7142, used in the present study, and includes restriction maps of this and subcloning vector, pAG-1542. A flow chart summarizing the construction of plasmid pAG-1542 is presented in FIG. 6.

B. Methods of Transforming Plants

The above-described chimeric genes can be inserted, for example, into plant cells. A transgenic plant containing a chimeric gene of the invention includes a raspberry E4 promoter operably linked to a heterologous gene, such as an nptII gene. Plants expressing the nptII gene product, i.e., neomycin phosphotransferase II, exhibit resistance to the anti-biotic, kanamycin.

In experiments performed in support of the invention, a chimeric RE4::nptII gene was inserted into tomato plant cells, and the resulting levels and patterns of expression of the nptII selectable marker gene were examined. Although nptII was selected as an exemplary marker gene to illustrate the ability of a raspberry plant promoter of the invention to regulate expression of a gene under its control, it will be understood that expression of any of a number of heterologous genes can be directed by the promoter of the present invention.

For example, nptI and nptII are different and distinct enzymes, with differences in both their amino acid sequences and substrate specificities (Beck, et al., 1982). The raspberry promoters of the invention are suitable for regulating expression of either of these neomycin phosphotransferases.

Plants suitable for transformation using a raspberry promoter of the invention include but are not limited to, raspberry, tomato, strawberry, banana, kiwi fruit, avocado, melon, mango, papaya, apple, peach, soybean, cotton, alfalfa, oilseed rape, flax, sugar beet, sunflower, potato, tobacco, maize, wheat, rice, and lettuce.

Chimeric genes containing a raspberry promoter, e.g., RE4pro, can be transferred to plant cells by any of a number of plant transformation methodologies. One such method, employed herein, involves the insertion of a chimeric gene into a T-DNA-less Ti plasmid carried by *A. tumefaciens*, followed by co-cultivation of the *A. tumefaciens* cells with plant cells.

As provided in Example 4, Agrobacterlum binary plant transformation vector, pAG-7142 is introduced into a disarmed strain of *A. tumefaciens* by electroporation (Nagel, et al., 1990), followed by co-cultivation with tomato plant cells, to transfer the chimeric genes into tomato plant cells.

In addition to Agrobacterium-based methods, alternative methodologies may be employed to elicit transformation of a plant host, such as leaf disk-based transformation, electroporation, microinjection, and microprojectile bombardment (particle gun transformation). These methods are well known in the art (Fry, et al., 1987; Comai and Coning, 1993; Klein, et al., 1988; Miki, et al., 1987; Bellini, et al., 1989) and provide the means to introduce selected DNA into plant genomes. Such DNA may include a DNA cassette which consists of a raspberry promoter (e.g., RE4pro) functionally adjacent a heterologous coding sequence.

Additionally, an iterative culture-selection methodology may be employed to generate plant transformants, and is particularly suited for transformation of woody species, such as raspberry. This method is described in detail in co-owned U.S. patent application Ser. No. 08/263,900, filed on Jun. 17, 1994, and entitled "Plant Genetic Transformation Methods and Transgenic Plants", and in co-owned U.S. patent application Ser. No. 08/384,556, filed on Feb. 3, 1995, also entitled "Plant Genetic Transformation Methods and Transgenic Plants". The contents of both of these applications are herein incorporated by reference.

In employing an iterative culture-selection transformation methodology, a chimeric gene of interest is inserted into cells of a target plant tissue explant, such as by co-culturing a target explant in the presence of Agrobacterium containing the vector of interest. Typically, the co-culturing is carried out in liquid for from about 1 to about 3 days. The plant tissue explant can be obtained from a variety of plant tissues including, but not limited to, leaf, cotyledon, petiole and meristem.

Transformed explant cells are then screened for their ability to be cultured in selective media having a threshold concentration of selective agent. Explants that can grow on the selective media are typically transferred to a fresh supply of the same media and cultured again. The explants are then cultured under regeneration conditions to produce regenerated plant shoots. These regenerated shoots are used to generate explants. These explants from selected, regenerated plant shoots are then cultured on a higher concentration of selective agent. This iterative culture method is repeated until essentially pure transgenic explants are obtained.

Pure transgenic explants are identified by dividing the regenerated plant shoots into explants, culturing the explants, and verifying that the growth of all explants is resistant to the highest concentration of selective agent used. That is, in the presence of selective agent there is no necrosis or significant bleaching of the explant tissue. Upon confirmation of production essentially pure transgenic explants, transgenic plants are produced by regenerating plants from the pure transgenic explants.

C. Identification and Evaluation of Plant Transformants

Transgenic plants are assayed for their ability to synthesize product mRNA, DNA, protein, and/or for their resistance to an aminoglycoside antibiotic, e.g., kanamycin. The assays are typically conducted using various plant tissue sources, e.g., leaves, stem, or fruit.

Leaf-based assays are informative if the raspberry promoter driving the heterologous gene (transgene) is at least somewhat active in leaf tissue, as is the case for promoters RE4. In such cases, leaf-based assays are useful for initial screens of the expression level of a transgene, since they can be performed much earlier than fruit-based assays. Fruit-based assays, on the other hand, provide more accurate data on transgene expression in a target tissue itself such as fruit.

RNA-based assays can be carried out using, for example, an RNAase protection assay (RPA). In carrying out such an assay, mRNA is typically extracted from plant cells derived from both transformed plants and wild-type plants. RNAse Protection Assays (RPA) can be performed according to the manufacturer's instructions using an "RPAII" kit from Ambion, Inc. (Hialeah, Fla.), as described by Lee, et al., 1987.

Gene expression patterns for transgenic plants containing chimeric genes regulated by a raspberry promoter can also be evaluated by conducting Northern dot blots. Promoter function (i.e., tissue and/or stage specific expression, or constitutive expression) can be evaluated by comparing northern blots of total RNA from leaf and fruit tissues at different ripening stages to northern blots of total RNA from various other plant tissues.

Experiments carried out in support of the invention indicate that the raspberry promoter, RE4pro, does not function as a stage or tissue-specific promoter. This is somewhat surprising, since the corresponding E4 promoter from tomato is both stage and tissue specific (Cordes, et al., 1989).

As further confirmation of expression of a downstream heterologous gene regulated by a raspberry promoter of the invention, a Western blot analysis can be carried out. In conducting a typical Western blot experiment, total soluble protein is extracted from frozen plant tissue and measured using, for example, the Coomassie Plus protein assay (Pierce, Rockford, Ill.). Known quantities of soluble protein, or known quantities of purified protein product (e.g., neomycin-phosphotransferase II, positive control) are resolved on a polyacrylamide gel and transferred to nylon membranes. The bound proteins were then probed with a monoclonal antibody specifically immunoreactive with the protein product.

In another approach for confirming gene expression directed by raspberry promoter of the invention, a Southern hybridization analysis is performed. Typically, plant DNA is extracted by grinding frozen plant tissue in extraction buffer, followed by centrifugation, separation of the resulting supernatant, and precipitation with cesium chloride. The resulting CsCl gradients are then centrifuged for an extended period of time (e.g., 48 h), and the recovered DNA is dialyzed and precipitated with ethanol. Upon recovery of plant DNA, the DNA is digested with suitable restriction enzymes to obtain DNA fragments, followed by electrophoretic separation on agarose gel. The resulting bands are transferred to nitrocellulose (Southern, 1975), and the blots are then probed with a labelled DNA fragment containing the nucleotide sequence of the transgene, to confirm the presence of DNA corresponding to a raspberry promoter-chimeric gene construct, as described above.

D. Comparative Evaluation of Gene Expression and Promoter Strength

Experiments performed in support of the invention demonstrate the transformation of tomato plants with a chimeric gene operably linked to a raspberry promoter of the present invention (e.g., RE4). As evident from the results of these experiments, the raspberry RE4 promoter is capable of providing expression of a gene placed under its control, and operates as a moderate level, constitutive promoter.

Tomato plants were transformed with plant transformation vector, pAG-7142, containing a raspberry promoter operably linked to an nptII gene (Example 4). As detailed in section III.A. above, plant transformation vector pAG-7142 contains the RE4::nptII gene. Chimeric genes containing either the hsp80 promoter or the CAS promoter (caulimovirus cassava mottle vein virus promoter) fused to the nptII gene were also prepared and used to transform tomato plants, to provide a comparative basis for evaluating performance of the raspberry promoters of the invention.

Results from ten separate transgenic events employing the constructs described above are provided in Example 5. To detect the presence of nptII enzymatic activity in plant transformants, protein extracts from leaf tissue of rooted plants available at the time of culture were assayed by ELISA. In some cases, only 1 plant was available for assay (e.g., Table 1, column 4, last two entries), while in other instances (e.g., Table 1, column 4, first entry), ten separate transgenic events were available for analysis.

In referring now to transgenic plants containing a raspberry E4 promoter, as can be seen from the results in Table 1, nptII enzymatic activity was detected in a high percentage of the plants assayed. Nine out of ten rooted plants transformed with a RE4::nptII chimeric gene tested positive for neomycin phosphotransferase. These results are comparable to those obtained for transgenic plants containing known promoter::nptII constructs, and indicate that the raspberry E4 promoter is effective to promote expression of heterologous genes placed under its control.

Also provided in Table 1 is a comparison of transformation frequency, that is, the ratio of the number of tissue explants producing regenerated shoots that are capable of rooting in the presence of selection agent to the total number of initial explants, expressed as a percentage. Based on the results in column III, and referring to plants containing a raspberry E4 promoter of the invention, on average, at least about seventy percent of the plants transformed with a raspberry promoter-containing construct survived selection with antibiotic, that is, they were capable of rooting in the presence of an amount of selection agent that would otherwise be toxic to non-transformed plant cells.

As in the case of the neomycin phosphotransferase assay discussed above, these results are consistent with those obtained with known plant promoters (hsp80, CAS), and further illustrate (i) the capability of the raspberry promoters of the invention to regulate expression of genes placed under their control, and (ii) the formation and use of chimeric gene constructs and transformation vectors containing a raspberry promoter (e.g., RE4), for transforming a plant host to form a transgenic plant expressing a heterologous gene. The raspberry E4 promoter provides constitutive expression of heterologous genes, as can be determined by the detection of nptII activity in all tissues obtained from transgenic plants transformed with the exemplary plant transformation vector, pAG-7142. Experiments carried out in support of the invention showed that the native RE4 gene is expressed at similar levels in different raspberry tissues, suggesting that the promoter, RE4pro, is capable of driving constitutive expression of heterologous genes placed under its control.

Promoter-driven expression of the nptII gene was evaluated by determining nptII enzyme levels in transformants. The results are presented in Table II and in FIG. 4. Protein levels for leaf tissue obtained from transformants containing the CAS::nptII chimeric gene are not included in either the table or the figure, since values from two CAS::nptII events assayed were in excess of 6000 pg/ml, indicating the high level of gene expression regulated by the CAS promoter (i.e., a strong promoter). The RE4 promoter directs transgene expression at levels similar to those observed for the hsp80 promoter, and is considered to be a moderate level promoter.

In looking at the results for the first two transgenic events in Table II, the average nptII enzyme level for RE4::nptII plants was about 25–30% that determined for CAS::nptII plants. A moderate promoter, such as RE4, drives expression of reporter genes at levels of about 2–50% those obtained with a strong promoter such as the CMV promoter.

In examining these same results, using the hsp80 promoter as a basis for comparison, the average nptII enzyme level determined for RE4::nptII plants was about 1.3–2.0 times higher than that determined for hsp80::nptII plants. A moderate strength promoter, such as RE4, drives expression of reporter genes at about 10–300% of the level obtained with a promoter such as the hsp80 promoter.

As supported by the data described above, the exemplary RE4 raspberry promoter described herein is capable of directing constitutive expression of a transgene at sufficient levels to support its use in regulating expression of any of a number of heterologous gene products.

Additionally, the transformation of tomato plants using the raspberry E4 promoter of the present invention illustrates that a promoter region derived from raspberry can be used to promote expression of a gene within plant cells from a completely different genus, family, or species of plant.

IV. Vectors of the Present Invention

The present invention provides vectors suitable for the transformation of plants. The vectors, chimeric genes and DNA constructs of the present invention are also useful for the expression of heterologous genes. Transgenic plants carrying the chimeric genes of the present invention may be a useful source of recombinantly-expressed material.

In one embodiment, the chimeric genes of the present invention have two components: (i) a constitutive promoter derived from a raspberry E4 gene, and (ii) a heterologous DNA sequence encoding a desirable product.

The vectors of the present invention may be constructed to carry an expression cassette containing an insertion site for DNA coding sequences of interest. The transcription of such inserted DNA is then under the control of a suitable raspberry promoter (e.g., a raspberry E4 promoter) of the present invention.

Such expression cassettes may have single or multiple transcription termination signals at the coding-3'-end of the DNA sequence being expressed. The expression cassette may also include, for example, DNA sequences encoding (i) a leader sequence (e.g., to allow secretion or vacuolar targeting), and (ii) translation termination signals.

Further, the vectors of the present invention may include selectable markers for use in plant cells (such as, a neomycin phosphotransferase II gene (nptII) or a neomycin phosphotransferase I gene). The presence of the nptII gene confers resistance to the antibiotic, kanamycin. Another aminoglycoside resistance gene for use in vectors of the invention includes a gene encoding hygromycin phosphotransferase, i.e., an hpt gene (Gritz, et al., 1983). Plant cells containing the hpt gene are able to grow in the presence of the amino-cyclitol antibiotic, hygromycin B. Other selectable marker sequences for use in the present invention include glyphosate-tolerant CP4 and COX genes (Zhou, et al., 1995). Transgenic plants expressing either of these genes exhibit tolerance to glyphosate, which can be used in selection media to select for plant transformants.

The vectors may also include sequences that allow their selection and propagation in a secondary host, such as sequences containing an origin of replication and a selectable marker. Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are also commercially available (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

The vectors of the present invention are useful for moderate level, constitutive expression of nucleic soacid coding sequences in plant cells. For example, a selected peptide or polypeptide coding sequence can be inserted in an expression cassette of a vector of the present invention. The vector is then transformed into host cells, the host cells are cultured under conditions to allow the expression of the protein coding sequences, and the expressed peptide or polypeptide is isolated from the cells. Transformed progenitor cells can also be used to produce transgenic plants bearing fruit.

The vectors, chimeric genes and DNA constructs of the present invention can be sold individually or in kits for use in plant cell transformation and the subsequent generation of transgenic plants.

A. Heterologous Genes

The methods and results described herein demonstrate the ability of a raspberry E4 promoter to provide constitutive, moderate level gene expression in transgenic plants. A raspberry promoter of the present invention includes a region of DNA that promotes transcription of the immediately adjacent (downstream) gene constitutively, in numerous plant tissues. According to methods of the present invention, heterologous genes are operably linked to a raspberry E4 promoter of the present invention.

Exemplary heterologous genes for the transformation of plants include genes whose products are effective to confer antibiotic resistance. Some of these genes, including the nptII gene, are described above.

Other genes of interest that can be used in conjunction with a raspberry promoter of the invention (e.g., RE4) include, but are not limited to, the following: genes capable of conferring fungal resistance, such as the polygalacturonase inhibiting protein (PGIP) gene from *Phaseolus vulgaris* (Toubart, et al., 1992) and modified forms of plant glucanase, chitinase (Jongedijk, et al., 1995) and other pathogenesis related (PR) genes (Melchers, et al., 1994; Ponstein, et al., 1994; Woloshuk, et al., 1991). These gene products (e.g., chitinases or beta-1,3-glucanases) can, for example, enhance resistance to fungi such as Fusarium, *Sclerotinia sclerotiorum*, and *Rhizoctonia solani*. Transformed plants expressing these products exhibit increased resistance to diseases such as seedling damping off, root rot disease, and the like. Other representative genes for conferring both viral and fugal resistance to transgenic plants are described in "VIRUS AND FUNGAL RESISTANCE: FROM LABORATORY TO FIELD" (Van Den Elzen, et al., 1994).

Additional exemplary heterologous genes for use with a raspberry promoter of the present invention include genes whose products are effective to confer herbicide-resistance to transformed plant cells. Exemplary herbicide resistance genes include a bialaphos resistance gene (bar) which codes for phosphinothricin acetyltransferase (PAT) (Akama, et al., 1995). Transgenic plants containing this gene exhibit tolerance to the herbicide, "BASTA". This gene can also be used as a selectable marker gene, since explants carrying the bar gene are capable of growing on selective media containing phosphinothricin (PPT), which is an active component of bialaphos.

Additional herbicide resistance genes include those conferring resistance to glyphosate-containing herbicides. Glyphosate refers to N-phosphonomethyl glycine, in either its acidic or anionic forms. Herbicides containing this active ingredient include "ROUNDUP" and "GLEAN". Exemplary genes for imparting glyphosate resistance include an EPSP synthase gene (5-enolpyruvyl-3-phosphosshikimate synthase) (Delanney, et al., 1995; Tinius, et al., 1995), or an acetolactate synthase gene (Yao, et al., 1995).

Other exemplary DNA coding sequences include a bxn gene encoding a bromoyxnil-specific nitrilase (Stalker, et al., 1988), under the transcriptional control of a raspberry E4 promoter. Transformed plants containing this chimeric gene express a bromoxynil-specific nitrilase and are resistant to the application of bromoxynil-containing herbicides.

Other gene products which may be useful to express using a RE4 promoter of the present invention include genes encoding a viral coat protein, to enhance coat-protein mediated virus-resistance in transgenic plants. Exemplary genes include genes coding for alfalfa mosaic virus coat protein (AlMV), cucumber mosaic virus coat protein (CMV), tobacco streak virus coat protein (TSV), potato virus coat protein (PVY), tobacco rattle virus coat protein (TRV), and tobacco mosaic virus coat protein (TMV) (Beachy, et al., 1990). Thus, a chimeric gene of the invention will contain a viral coat protein gene, such as an ALMV, CMV, TSV, PVX, TRV, or TMV gene, under the transcriptional control of a raspberry E4 promoter.

Additional heterologous genes for use with a raspberry promoter of the present invention include genes encoding a dominant defective protein, such as for example, mutant forms of the ETR1 gene. Mutant forms of the ETR1 gene of *Arabidopsis thaliana* confer insensitivity to ethylene (Schaller, 1995; Chang, et al., 1993).

Other heterologous genes which may be operably linked to the RE4 promoter, for expression in plant cells, include genes capable of altering a plant bio-chemical pathway, such as the ACCD gene. The ACCD gene forms a product, 1-aminocyclopropane-1-carboxylic acid deaminase, which degrades a precursor in the ethylene biosynthetic pathway (Reed, et al., 1996).

B. Expression in Heterologous Plant Systems

Experiments performed in support of the present invention demonstrate the versatility of the chimeric gene constructs of the invention. The vector constructs of the present invention can be used for transformation and expression of heterologous sequences in transgenic plants independent of the original plant source for the promoter sequence. For example, the RE4-nptII chimeric gene was introduced into tomato plant cells.

These data suggest that a raspberry E4 promoter is useful for promoting gene expression in heterologous plant systems, i.e., plant cells other than raspberry, such as tomato. Further, the expression mediated by such raspberry promoters appears to be constitutive, even in heterologous plants. These findings support the usefulness of the vectors, chimeric genes and DNA constructs of the present invention for transformation of plants.

V. Utility

Experiments performed in support of the present invention demonstrate that the gene expression patterns for nptII, directed by an RE4 promoter, are observed in various plant tissues (e.g., leaf, stem, fruit, root). Accordingly, use of a raspberry E4 promoter allows constitutive expression of a foreign gene placed under its control.

A raspberry E4 promoter of the invention, e.g., RE4, can be cloned as described above employing sequence information described herein. A raspberry E4 promoter can be used to express any heterologous gene whose function would be enhanced or enabled by a moderate level, constitutive promoter. Exemplary genes are described above.

The use of a RE4 promoter cannot be considered limited to raspberries, particularly in view of the successful transformation of tomato using the exemplary raspberry promoter, RE4. Since raspberry is essentially a miniature drupe fruit, it is likely that the raspberry E4 promoter will function in other drupe fruits. The constructs and methods of the present invention are applicable to all higher plants including, but not limited to, the following: Berry-like fruits, for example, Vitis (grapes), Fragaria (strawberries), Rubus (raspberries, blackberries, loganberries), Ribes (currants and gooseberries), Vaccinium, (blueberries, bilberries, whortleberries, cranberries), Actinida (kiwifruit and Chinese gooseberry). Further, other drupe fruits, including, but not limited to, Malus (apple), Pyrus (pears), most members of the Prunus genera, sapota, mango, avocado, apricot, peaches, cherries, plums, and nectarines. Additional plant sources are described above.

The present invention provides compositions and methods to regulate plant cell expression of any gene in a constitutive manner. In one embodiment, the promoters of the present invention can be used to regulate expression of a selectable marker gene, such as nptII. Alternatively, a raspberry E4 promoter can be used to promote expression of a herbicide-resistance gene, or to regulate expression of a gene encoding a viral coat protein, to provide enhanced virus resistance.

A raspberry E4 promoter, that is, a promoter capable of promoting expression of a raspberry E4 gene, can be used in chimeric genes, plant transformation vectors, expression cassettes, kits, and the like, to promote transformation of plant cells.

The raspberry promoter described herein may also be employed in a method for providing moderate level expression of a heterologous gene, such as a selectable marker gene, in a transgenic plant.

The following examples illustrate, but in no way are intended to limit the scope of the present invention.

Materials and Methods

Biological reagents were typically obtained from the following vendors: 5' to 3' Prime, Boulder, Colo.; New England Biolabs, Beverly, Mass.; Gibco/BRL, Gaithersburg, Md.; Promega, Madison, Wis.; Clontech, Palo Alto, Calif.; and operon, Alameda, Calif. Standard recombinant DNA techniques were employed in all constructions (Adams and Yang, 1977; Ausubel, et al., 1992; Hooykaas and Schilperoot 1985; Sambrook, et al., 1989; Wang, et al., 1990; Kawasaki, et al., 1989; Veluthambi, et al., 1988; Benvenuto, et al., 1988).

EXAMPLE 1

Isolation of a Genomic Clone of a Raspberry E4 Gene

A. Preparation of an E4 Probe

A probe was prepared according to standard methods (Maniatis, et al., 1982). The probe was a ~740 bp polymerase chain reaction (PCR; Mullis, 1987; Mullis, et al., 1987) product amplified from genomic tomato DNA using PCR primers designed according to Cordes, et al. (1989). The 5' primer sequence (E4G5 #72), corresponding to the region between nucleotides 1439 and 1452 of the tomato E4 gene (SEQ ID NO:5), is represented herein as SEQ ID NO:6. The 3' primer sequence (E4G3 #73), corresponding to the region between nucleotides 2160 and 2177 of the E4 gene (SEQ ID NO:5), is represented as SEQ ID NO:7. The probe was generated by random priming using a kit from B öhringer Mannheim (Indianapolis, Ind.), according to the manufacturer's instructions.

B. Southern Blot Analysis

A Southern blot analysis was conducted to investigate the presence of E4 gene sequences in other plant species. The blot consisted of HindIII digests of six genomic plant DNAs: tomato, raspberry, strawberry, melon, carnation and cauliflower, along with size standards.

This blot was hybridized with the tomato E4 probe described in Example 1.A. above, following standard methods (Maniatis, et al., 1982). Several bands were apparent in each lane, with the lane corresponding to tomato DNA showing the strongest signal.

C. Screening of a Raspberry Genomic Library

A raspberry genomic library in lambda GEM-11 was obtained from Novagen (Madison, Wis.) and screened by standard methods with the E4 gene probe described in 1.A. above. Four lambda clones which hybridized to the probe were identified. The clones were purified by 3 rounds of plaque purification. One of the clones (λ4) was selected for further analysis.

D. Analysis of a Positive Clone

The clone was digested with several enzymes (ApaI, BamHI, EcoRI, HindIII, NcoI, SacI, and SalI), run on a gel, and transferred to a "SUREBLOT" nylon membrane (Oncor, Gaithersburg, Md.). The blot was hybridized overnight at 42° C. with the tomato E4 probe in "HYBRISOL I" hybridization cocktail (Oncor, Gaithersburg, Md.). The final (and most stringent) wash was 0.1×SSC, 0.1% SDS for 30 minutes at room temperature (22° C.).

A 1.6 kb SacI fragment which hybridized to the probe was subcloned into pGEM5Zf(+) (Promega, Madison, Wis.) and further characterized. A 225 bp region in that fragment was found to be highly homologous to the tomato E4 gene at both the DNA level (74%) and the amino acid level (80%). The sequence of this region (SEQ ID NO:9) was compared to the sequence of a portion of the tomato E4 gene (SEQ ID NO:5).

Additional raspberry E4 gene sequences were obtained by further hybridization screening of raspberry genomic library clones. The sequence of a genomic copy of a raspberry E4 gene is presented in FIGS. 1A–1D (nucleotide sequence: SEQ ID NO:2; polypeptide sequence: SEQ ID NO:8).

EXAMPLE 2

Isolation of a Raspberry E4 Promoter (RE4P) and Construction of Plasmid pAG-471

A 1.06 kb HindIII and SacI-digested Raspberry E4-containing fragment derived from a lambda clone described in Example 1 was purified by running the fragment on a 1% low melting point agarose gel (SeaPlaque, FMC BioProducts, Rockland, Me.). The 1.06 kb HindIII to SacI fragment, containing the 0.95 kb RE4pro promoter region was cut from the body of the gel. The DNA fragment was then purified away from the gel using β-agarase from NEB, according to the manufacturer's instructions. The sequence of the 0.95 kb RE4 promoter region, i.e., RE4pro, is presented herein as SEQ ID NO:1, and is also illustrated as FIG. 5.

Cloning vector, pUC-19 (Clontech Laboratories, Palo Alto, Calif.), was digested with HindIII and SacI. The 2.6 kb fragment from pUC-19 and the 0.95 kb RE4pro promoter fragment were combined in a ligation reaction, using Gibco/BRL's T4 DNA ligase, following manufacturer's instructions, to form the plasmid pUC-RaspE4(H3-Sac). A schematic representation of the construction of plasmid pUC-RaspE4(H3-Sac) is shown in FIG. 2.

Cloning vector pGEM®3Zf(+) (Promega, Madison, Wis.) was digested with XbaI and BamHI. The digested plasmid was run on a 1% low melting point agarose gel (SeaPlaque, FMC BioProducts, Rockland, Me.). The gel region containing the 3.2 kb fragment was cut from the body of the gel. The DNA fragment was then purified away from the gel using β-agarase from NEB, following the manufacturer's instructions.

The plant binary transformation vector pGPTV.kan (Max-Planck Institut, Köln, Germany) was digested with XbaI and BamHI. The digested plasmid was run on a 1% low melting point agarose gel (SeaPlaque, FMC BioProducts, Rockland, Me.). The gel region containing the 1.48 kb nos::nptII fragment was cut from the body of the gel. The DNA fragment was then purified away from the gel using β-agarase from NEB, following the manufacturer's instructions. The gel region containing the 13.3 kb fragment was discarded.

The 3.2 kb fragment from pGEM®3Zf(+) and the 1.48 kb nos::nptII fragment were combined in a ligation reaction, using Gibco/BRL's T4 DNA ligase, following manufacturer's instructions to form the intermediate plasmid pAG-411.

A 1 kb fragment of the raspberry E4 promoter, contained within subclone pUC-RaspE4 (H3-Sac), was PCR amplified using primers NEB #1233 (SEQ ID NO:3) and RE4proApaI (SEQ ID NO:4) under the following PCR reaction conditions:

One cycle at 97° C. for 4 minutes, after which the AMPLITAQ was added;

Two cycles at 97° C. for 1 minute, 54° C. for 1 minute and 72° C. for 1 minute;

25 cycles at 94° C. for 1 minute, 54° C. for 1 minute and 72° C. for 1 minute;

One cycle at 72° C. for 5 minutes, followed by cooling to 5° C.

This fragment was then purified from the reaction mixture as follows. The PCR reaction mixture was transferred to a light Phase Lock Gel tube (5 Prime to 3 Prime, Boulder, Colo.) Phenol:Chloroform:Isoamyl Alcohol (25:24:1) was added to this tube at a volume equal to the PCR reaction volume. The tube was spun in a micro-centrifuge following the manufacturer's instructions. The upper, aqueous phase was transferred to a Select, G-50 spin column (5 Prime to 3 Prime, Boulder, Colo.) and the DNA centrifuged through the column following the manufacturer's instructions. To the eluant was added 1/10 volume of 3M sodium acetate and 2.5 volumes of ethanol in order to precipitate the DNA. The sample was incubated on ice for $\geq$10 minutes, and then micro-centrifuged at 4° C. for 30 minutes at 14,000 rpm. The supernatant was decanted from the tube and the pellet washed twice with 75% ethanol. The pellet was allowed to dry. Subsequent to drying, the pellet was resuspended in 25 $\mu$l ½ strength TE (5 mM Tris-HCl, 0.5 mM EDTA, pH 8). This fragment was digested to completion with restriction enzymes HindIII and ApaI to produce an RE4 promoter fragment. This fragment was purified in the same manner as the PCR product described above.

The 4 kb fragment from pAG-411 and the 0.95 bp RE4 promoter fragment derived from pUC-RaspE4(H3-Sac) were combined in a ligation reaction, using Gibco/BRL's T4 DNA ligase, according to the manufacturer's instructions to form the intermediate vector pAG-471. FIG. 2 represents a schematic representation of the steps involved in constructing plasmid pAG-471.

EXAMPLE 3

Chimeric Genes Containing the RE4 Promoter Construction of a RE4pro:nptII Binary Plant Transformation Vector An Agrobacterium binary vector containing the chimeric RE4pro-nptII gene was constructed as follows, for use in plant transformation experiments. FIG. 3 represents a flow chart outlining the construction of one *Agrobacterlium tumefaciens* binary vector, pAG-7142, used in the present study, and includes restriction maps of this and subcloning vector, pAG-1542. The Agrobacterium Ti right and left borders are abbreviated $B_R$ and $B_L$, respectively in FIG. 3.

A. Construction of Plasmid pAG-1542

Figure 6:
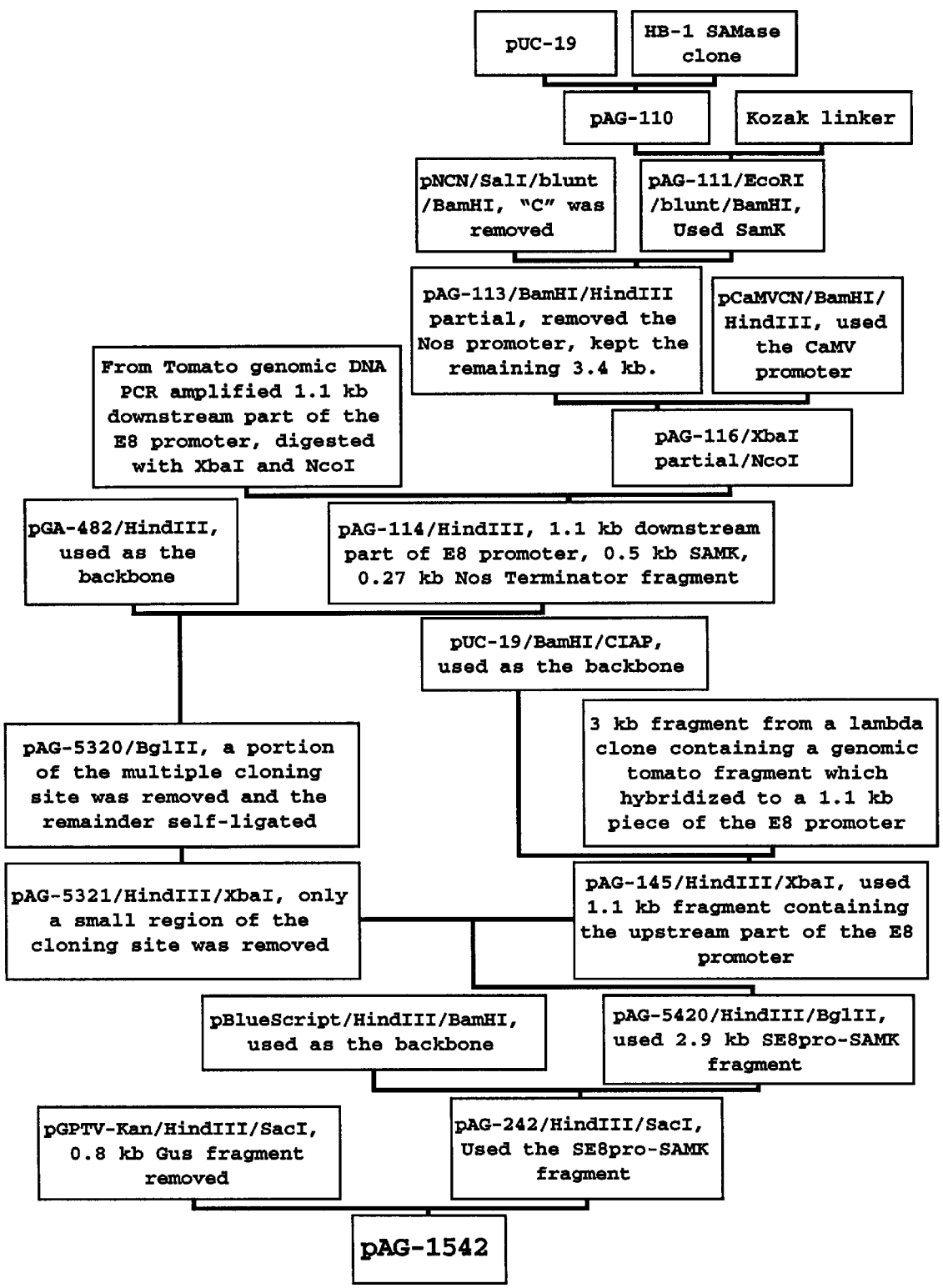
FIG. 6 is a flow chart summarizing the construction of plasmid pAG-1542.
Figure 7:
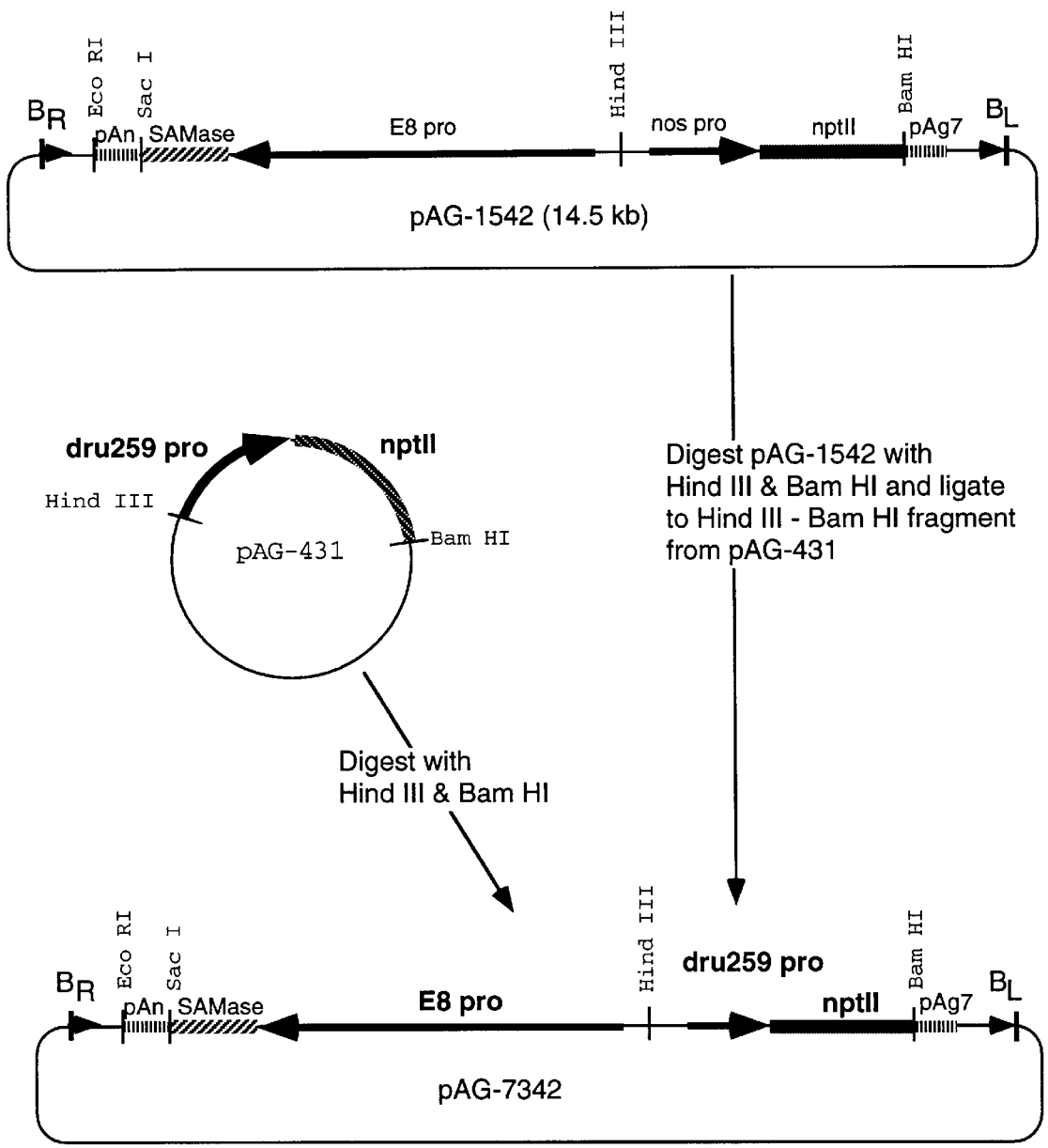

A flow chart summarizing the construction of plasmid pAG-1542 is illustrated in FIG. 6. Plasmid pAG-1542 was constructed using conventional cloning techniques known in the art (Sambrook, et al., 1989). Subcloning binary vector pAG-1542 contained the nptII marker gene under the control of the nos promoter located near the left border and the SAMase gene (Ferro, et al., 1995) driven by the tomato E8 promoter (Deikman, et al., 1988; Deikman, et al., 1992) located near the right border.

B. Construction of Binary Plant Transformation Vector, pAG-7142

Plasmid pAG-471, described in Example 2, was digested with BamHI and HindIII, and a resulting 1.8 kb RE4::nptII fragment was purified by isolation from a 1% "SEA-PLAQUE" agarose gel, using NEB $\beta$-agarase. This fragment was inserted into plasmid pAG-1542, which had been digested with restriction enzymes BamHI and HindIII to excise the nos pro::nptII fragment. The resulting binary vector, designated pAG-7142, contained the RE4 promoter fused to the nptII gene. Construction of the Agrobacterium binary plant transformation vector, pAG-7142, is presented schematically in FIG. 3.

EXAMPLE 4

Plant Transformation With an RE4-nptII Binary Vector

A cherry tomato line (CH3) obtained from Sunseeds Co. (Morgan Hill, Calif.) was used as the target for plant transformation experiments. Transformation was carried out using a standard cotyledon-based Agrobacterium co-cultivation method (Fillatti, et al., 1987), as described below.

*Agrobacterium tumefaciens* strain EHA101 (Hood, et al., 1986), a disarmed derivative of *Agrobacterium tumefaciens* strain C58, was used to introduce coding sequences into plants. This strain contains a T-DNA-less Ti plasmid. The pAG-7142 plasmid was transferred into EHA101 using electroporation essentially as described by Nagel, et al. (1990). Briefly, an *Agrobacterium tumefaciens* culture was grown to mid-log phase (OD 600 0.5 to 1.0) in MG/L agar media containing tryptone (5 g/l), yeast extract (2.5 g/l), NaCl (5 g/l), mannitol (5 g/l), sodium glutamate (1.17 g/l), $K_2HPO_4$ (0.25 g/l), $MgSO_4$ (0.1 g/l) and biotin (2 $\mu$g/l), adjusted to pH 7.2 by addition of sodium hydroxide.

Tomato cotyledon tissue explants were excised from both the tip and base of the cotyledon. Cotyledon explants were pre-conditioned for 2 days on tobacco feeder plates (Fillatti, et al., 1987). The pre-conditioned explants were inoculated with EHA101 containing the pAG-7142 plasmid and finally placed in a 10 ml overnight culture of EHA101/pAG7142 for 5 minutes. The explants were then co-cultivated with the EHA101 strains for 2 days on tobacco feeder plates as described by Fillatti, et al. (1987).

The explants were grown in tissue culture media containing 2Z media (Fillatti, et al., 1987), Murisheegee and Skoog (MS) salts, Nitsch and Nitsch vitamins, 3% sucrose, 2 mg/l seatin, 500 mg/l carbenicillin, 60–200 mg/l kanamycin, and 0.7% agar. The explants were grown in tissue culture for 8 to 10 weeks. The carbenicillin treatments were kept in place for 2 to 3 months in all media. The explants and plants were kept on carbenicillin until they were potted in soil as a counter-selection to rid the plants of viable *Agrobacterium tumefaciens* cells.

Table 1 presents a summary of the plant transformation experiments, including concentrations of selection agent utilized, and transformation frequencies. Results obtained for plant transformation experiments using the novel raspberry promoters of the present invention are compared to those obtained using binary vectors containing two different strong constitutive promoters, a caulimovirus promoter, the cassava mottle vein virus promoter (CAS) and the hsp80 promoter. The CAS promoter was obtained from The Scripps Research Institute (La Jolla, Calif.). Isolation of the hsp80 promoter, its nucleotide sequence, as well as vector constructions and expression levels of transgenes containing the hsp80 promoter have been described (Brunke and Wilson, 1993).

EXAMPLE 5

Relative Expression of the nptII Marker Gene in Transgenic Plants Containing Promoters Derived From Raspberry Leaf tissues from 10 separate transgenic events employing vector, pAG-7142, containing a raspberry E4 promoter described herein (RE4) were assayed by ELISA to determine nptII expression levels, according to the manufacturer's (5'–3', Inc., Boulder, Colo.) recommended protocols for (i) protein extraction and (ii) determination of nptII expression levels. Results from the transformation experiments are provided in Tables I and II below.

The nptII assay was carried out with a few samples using rooted plants which were available in culture at the time of testing. Thus, not all rooted plants were tested for nptII expression. The results of the ELISA assay are presented in column (IV) of Table I below.

TABLE 1

Transformation Results

| (I) Promoter | (II) Selection Conc. of kanamycin (mg/l) | (III) Transformation Frequency | (IV) nptII Expression |
|---|---|---|---|
| CAS | 200 | 50% | 100% (10/10) |
| RE4 | 90 | 72% | 90% (9/10) |
| hsp80 | 60 | 50% | 63% (5/8) |
|  | 90 | 27% | 100% (1/1) |
|  | 200 | 60% | 100% (1/1) |

In referring to the data presented in Table I, transformation frequency is defined as the ratio of the number of tissue explants producing regenerated shoots that are capable of rooting in the presence of selection agent (kanamycin) to the total number of initial tissue explants, expressed as a percentage. NptII expression level, expressed as a percentage, is the ratio of nptII positive plants to the total number of rooted plants tested for nptII, based upon the results of the ELISA assay described in Example 5. A positive nptII result is an ELISA value greater than background. For example, the first entry under column (IV) indicates that out of 10 events tested for nptII, 10 exhibited positive ELISA results.

Relative expression levels of nptII are presented in Table II. The data from transgenic plants containing the CAS::nptII construct are not included in Table II due to the high expression levels observed in transformants containing the CAS promoter. Values from the two CAS::nptII events assayed were in excess of 6000 pg/ml of nptII.

Figure 4:
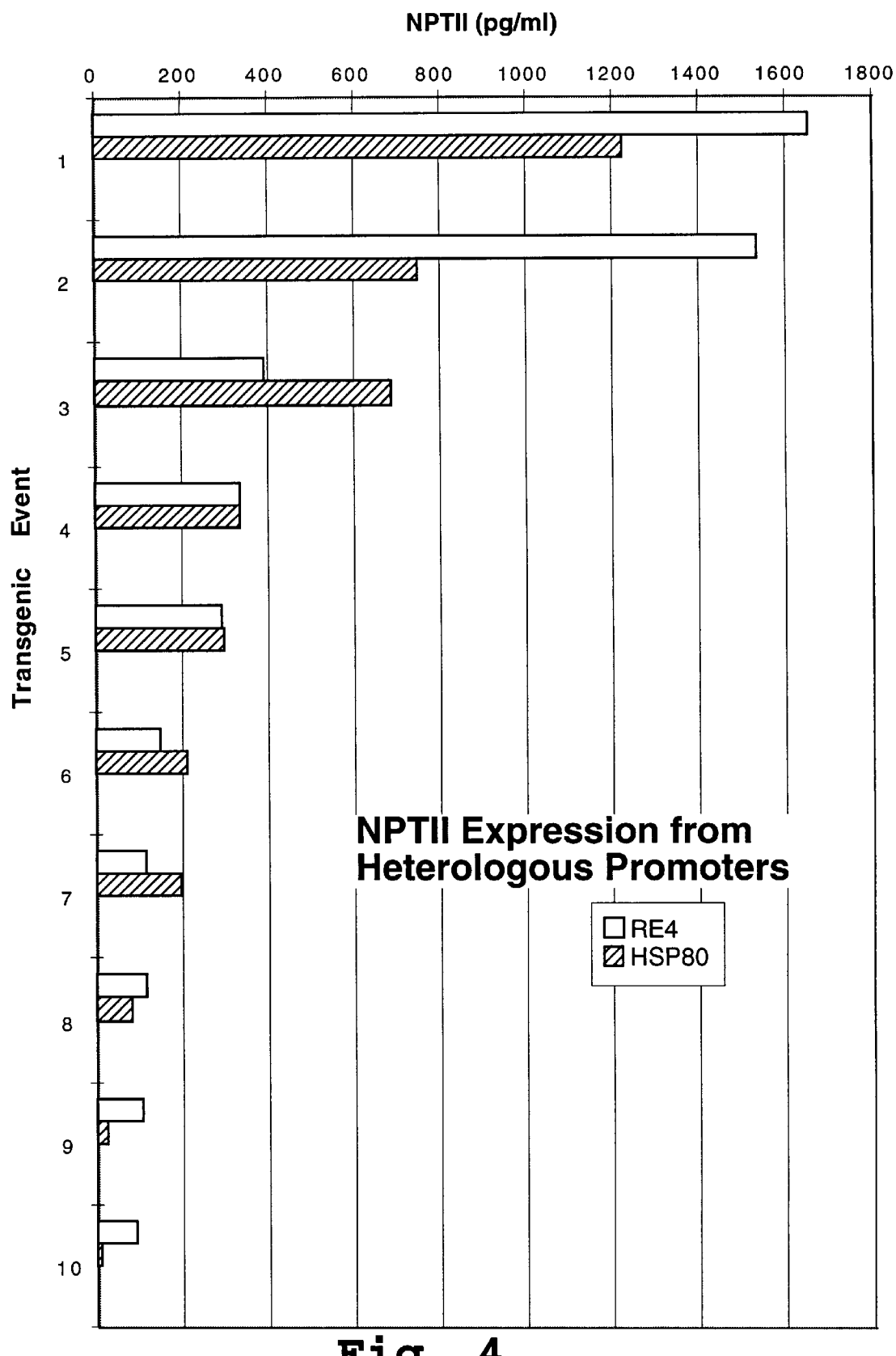
FIG. 4 is a graph representing relative levels of nptII gene expression across 10 transgenic events for two different promoter-npt II chimeric gene combinations.

The range of expression across events presented in Table II below as well as illustrated graphically in FIG. 4 is typical for transgene expression in plants.

TABLE 2

Expression of nptII (pg/ml)

| Transgenic Event | Promoter RE4 | hsp80 |
|---|---|---|
| 1 | 1654.54 | 1223 |
| 2 | 1533.64 | 748.7 |
| 3 | 391.6 | 687.3 |
| 4 | 333.94 | 332.1 |
| 5 | 289.3 | 294.9 |
| 6 | 147.94 | 207.5 |
| 7 | 112.6 | 194.4 |
| 8 | 112.6 | 79.12 |
| 9 | 103.3 | 21.46 |
| 10 | 92.14 | 10.3 |

The data above indicate that the RE4 and hsp80 promoters have similar expression strengths, that is, they effect moderate level expression of heterologous genes placed under their control. Additionally, the exemplary raspberry promoter of the invention, RE4, is capable of expressing sufficient levels of nptII to allow selection of transgenic plants.

While the invention has been described with reference to specific methods and embodiments, it will be appreciated that various modifications and changes may be made without departing from the invention.

---

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 946 base pairs
      (B) TYPE: nucleic acid
      (C) STRANDEDNESS: both
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (C) INDIVIDUAL ISOLATE: DNA sequencee of raspberry E4 promoter (xi) SEQUENCE DESCRIPTION: SEQ ID NO:1:

AAGCTTAATT GAGATGATTA GCCCAGACCC AGCAGGATTA GGCTTAATGG TGGTCCATTT     60

GAGAAAAAGA TTAAAAATGA TGTCATAAAA AAACGTGGTC GGCAGGATTC GAACCTGCGC    120

GGGCAAAGCC ACATGATTTC TAGTCATGCC CGATAACCAC TCCGGCACGA CCACAATGAT    180

GCTACAATTG CTTTGTTGTA ATCATTAACT TATGGTTGAG TTTGATGCTG ATTAATACTA    240

TTATGTTTCC ATTAACTACT TTTGAAGTAT ACAAAATTAC GAATTTATAA CCAAATTTGA    300

GGTATAATAT GCGAGAGCTA CCTAAATTTT TCTTACTTAA TTTTAAAGTA CATTCAAATT    360

CTGAATTTAT ATTGTGTATA GTCAGAAAAC AATCTACATA TTTAAACACA TAAATTTCTC    420

ACGTTTATAA TCAATTTTGT CGGTTCCTGT AATTTTTCTA AAATAAAAAG CAACCAAAAT    480

TGTGCATCAA CTTATTACAT ACCATGGGAA ATGCAAACTT CAAAACTTAT GGACTCAAAG    540

GGTACATATC TAAACTACAT ATTGTCAGAT TCTTCACTCT TATTTCTTGA GGGCCTCGAG    600

GCATTACCAA CCAAATCCAA AAATTGCTTT CGAATCTCAA TAAAAGGAT AACCCCATGA     660

AAAAGACGTG GACGGCAGGA TTCGAACCTG CGCGCAGAGC CCACATGATT TCTAGTCATG    720

CCCGATAACC ACTCCGGCAC GTCCACTTCA CTGTTAACGT TTACAGTAAC AAGTCACTAA    780

CTACTAATCA ACATTAGCTC AGGAAATCAA AACTAGATTA TTTACATTTA CAACGACATG    840

TCGTTCGAAG TAGTTGGTCT GTATCTGAGT AGCTTTGGCG GGTAGATTCA ATCGCATTTC    900

TGCATATAAA ACTGATCCTC CCTCTATCGC CAAAGTCAAA CTGAAA                  946

(2) INFORMATION FOR SEQ ID NO:2:

(i) SEQUENCE CHARACTERISTICS:
        (A) LENGTH: 2715 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: DNA sequence of isolated E4 gene
             from rasp genomic library (xi) SEQUENCE DESCRIPTION: SEQ ID NO:2:

AAGCTTAATT GAGATGATTA GCCCAGACCC AGCAGGATTA GGCTTAATGG TGGTCCATTT     60

GAGAAAAAGA TTAAAAATGA TGTCATAAAA AAACGTGGTC GGCAGGATTC GAACCTGCGC    120

GGGCAAAGCC ACATGATTTC TAGTCATGCC CGATAACCAC TCCGGCACGA CCACAATGAT    180

GCTACAATTG CTTTGTTGTA ATCATTAACT TATGGTTGAG TTTGATGCTG ATTAATACTA    240

TTATGTTTCC ATTAACTACT TTTGAAGTAT ACAAAATTAC GAATTTATAA CCAAATTTGA    300

GGTATAATAT GCGAGAGCTA CCTAAATTTT TCTTACTTAA TTTTAAAGTA CATTCAAATT    360

CTGAATTTAT ATTGTGTATA GTCAGAAAAC AATCTACATA TTTAAACACA TAAATTTCTC    420

ACGTTTATAA TCAATTTTGT CGGTTCCTGT AATTTTTCTA AAATAAAAAG CAACCAAAAT    480

TGTGCATCAA CTTATTACAT ACCATGGGAA ATGCAAACTT CAAAACTTAT GGACTCAAAG    540

GGTACATATC TAAACTACAT ATTGTCAGAT TCTTCACTCT TATTTCTTGA GGGCCTCGAG    600

GCATTACCAA CCAAATCCAA AAATTGCTTT CGAATCTCAA TAAAAGGAT AACCCCATGA     660

AAAAGACGTG GACGGCAGGA TTCGAACCTG CGCGCAGAGC CCACATGATT TCTAGTCATG    720

```
CCCGATAACC ACTCCGGCAC GTCCACTTCA CTGTTAACGT TTACAGTAAC AAGTCACTAA      780

CTACTAATCA ACATTAGCTC AGGAAATCAA AACTAGATTA TTTACATTTA CAACGACATG      840

TCGTTCGAAG TAGTTGGTCT GTATCTGAGT AGCTTTGGCG GGTAGATTCA ATCGCATTTC      900

TGCATATAAA ACTGATCCTC CCTCTATCGC CAAAGTCAAA CTGAAAATGG CTTCCACCAC      960

CACCAACAAC CCAGCTCTAG ACCCAGATTC GGACACTCCG GATAATCCGG GTCACGAGTT     1020

TGCTCAATTC GGATCCGGGT GCTTCTGGGG AGCCGAGCTC AGGTTTCAGC GAGTGGCCGG     1080

TGTGGTCAAG ACCGAGGTTG GGTACTCCCA GGGCCACGTC CACGATCCGA ATTACAAACT     1140

GGTCTGCTCC GGAACTACCA ACCATTCGGA GGTCGTTCGG GTCCAGTTCG ACCCGCAAGT     1200

CTACCCATAC TCGGACCTGC TTTCCGTCTT TTGGTCTCGT CATGATCCAA CGACTGTCAA     1260

TCGCCAGGTA TGGGGATTGG GGACTTCTGT TTTCATTTGA ATTTTGATGC TAAAAAATTT     1320

CTTGCTTTTT CATACTACAC AGTACACACA AAAAGTTGTG TTTTTTTTTC ATTCTTTTAA     1380

ATAGTAGTTG GAAAAGTGCT CTTGGAGTTG AAGAGTACTT CAGTATTGCA TATGGTCTCA     1440

GTGAAATTGA TAGTGATTAA TCATAAGGAT GTTTGTGATT AAAGGCAGGA TGCATTTTGT     1500

GTATGANTGA TTTTGGGTAG AATATTTTTG GAACAGTTAA AATTTATGGG CTGCTGCACA     1560

CTGGCTATGA ACAAATGTAT AGCATTAAAG TGCTTATGAC AAATTCACAA TTGTATATTA     1620

GCAGCAGAGA CATTAAAGTT TCTAAATGCC TTTTAAGTAG TTGGAAAAAA GTGCTTTTTT     1680

TGGTTGAAGA AGCACATTCA CTATTTGCCT GTTAATGGAA TTGGTAATGA TGAATCACAA     1740

GGATATTTGT GAATACAAGC AGGATGCTTT TAGTGTGCAA GTGATCTTTC GGAACATTTA     1800

AAATGTATAA CAAAGGTGTA ACATAAGAAG GCTTTGAAAT ATTCTCAATT TCTCATTGAT     1860

TGAATGAATT ATGTGTTAGG GTGGAGATGT GGGTACTCAA TATCGATCTG GAATATACTA     1920

CTACAACGAA ACGCAGGCCC GTCTAGCACA GGAATCAAAG GAAGCAAAGC AACTGGAGTT     1980

TAAGGATAAG AAGGTGGTGA CAGAGATTCT TCCAGCAAAG AGGTTTTACA GGGCAGAGGA     2040

GTACCATCAG CAATATCTCG CAAAGGGAGG AGGTAATGGC AACAAACAAT CTGCTGAAAA     2100

AGGTTGCAAT GATCCTATTC GATGCTATGG TTGAGAAACT AATGCATTAT GCCATTATTA     2160

AAACTCTACT GGTTTACTAT GCAGAAACAC CTATGTCAGT TCAATTATAC TGAAGGCACC     2220

AAAGTGTCAT CTTAAATTAT ATGGCAATGT TTTACTCGTT ATGAATAAAG GAGGTCCAAG     2280

TCGACCAGAT ATGAACAAAT GAAATATTGC CATGTTAATT GGAATCCAGT AGTAATTAGG     2340

ATTTGTTTTG GTGTATGTAC TCCGATATCA GATATGCAAA TGATGCATTG TGTTTTTATA     2400

TATTGACAAG TTCCAAATTA TAGTACTTCG TATGTGTTAT GCGGTTTAAT TAGTGTTGCT     2460

TACTTGAATG GTATATTACT ATTATGCTTA GTAGGAACTA GGAACTAGGG AATATGTTGT     2520

GATAGAGTTG TCCAACGAAA TTTTTGACCA AAGTTATTTC ATTGAATAAA AACTACAGAT     2580

CTTAGAGATA CATCCAATTC TATAAAGTGA AAGAAGCAAA TATTATTTGT TCATGAGGCT     2640

ATGAGTCATG AACTTTATGC TATAACCGAA GCAACCTCAG AAAAGTCGAA GTAAATTGTG     2700

TATTGTTTAG AGCTC                                                    2715
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: primer NEB#1233

(xi) SEQUENCE DESCRIPTION: SEQ ID NO:3:

AGC GGA TAA CAA TTT CAC ACA GGA                                      24

(2) INFORMATION FOR SEQ ID NO:4:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: primer RE4 proApaI (xi) SEQUENCE DESCRIPTION: SEQ ID NO:4:

GGG GGC CCT TTT CAG TTT GAC T                                        22

(2) INFORMATION FOR SEQ ID NO:5:

(i) SEQUENCE CHARACTERISTICS:
              (A) LENGTH: 2796 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (C) INDIVIDUAL ISOLATE: tomato E4 gene DNA (ix) FEATURE:
              (A) NAME/KEY: CDS
              (B) LOCATION: 1439..1774

(ix) FEATURE:
              (A) NAME/KEY: exon
              (B) LOCATION: 1439..1774

(ix) FEATURE:
              (A) NAME/KEY: CDS
              (B) LOCATION: 1859..2113

(ix) FEATURE:
              (A) NAME/KEY: exon
              (B) LOCATION: 1859..2113

(ix) FEATURE:
              (A) NAME/KEY: intron
              (B) LOCATION: 1775..1858

(xi) SEQUENCE DESCRIPTION: SEQ ID NO:5:

GAATTCTCAA TTGAGCCCAA TTCAATCTCC AATTTCAACC CGTTTTAAAA CTTTTTATTA      60

AGATATGTTT CTATATTGAA AGTATGAATT ATTATCTATT TAACATCTTT TAGGATTTAT     120

CTATCCATTT GCTACTTTTT TAACAAAAAA TTCTTGAGTG AAAATTCAAA TTGTGATTAT     180

AAAAGTTAAA TATCAATATG TTAAATTATT AAGATTAATC GGGTCAAATT GGCGGGTCAA     240

```
GGCCCAATTC TTTTTTAGCC CATTTAAGCT CAAAGTAAAC TTGGGTGGGT CAAGACCCAA      300

CTCGATTTCT GTTCAACCCA TTTTAATATT TCTATTTTCA ACCTAACCCG CTCATTTGAT      360

ACCCCTACAA ATATCATATT TGTGTGTGAA ATATTTTTTG GGCTGGAGAG AGAGGCCCCG      420

AGGGGAGTGG AGGGGTGGGG TGGGGAGAGA GAGCGAGAAA GAGTGGAGAG AGAAATTTGA      480

TATGAAATCC TACATATATT ACAGATTGTA ATGTTCTAAA CTATAACGAT TTGTCATAAA      540

CACATATCAT GGATTTGTCT TTTTGTGTAA TTTTCCCAAT TGTAAATAGG ACTTCGTTAT      600

TTGAAACTTG AAAGTGAAGT CACATAGATT AAGTACAAAC ATTAATTAAA GACCGTGGTG      660

GAATGATAAA TATTTATTTA TCTTTAATTA GTTATTTTTT TGGGAGCTCT TTATTCCAAT      720

GTGAGACTTT TGCGACATAT ATTCAAATTT AATCGAATCA CAATATGTAT TAGATTGATA      780

AAAAAATAAT TTTTTTACAA TGTTAGTTGA GACTCATAAC TTACTGCCTA TTGGTAATCT      840

ATGACTCCTA ATTCCTTAAT TATTTAAATA TATCATCTTG ATCGTTAACA AAGTAATTTC      900

GAAAGACCAC GAGTAAGAAG ACAAACGAGA ATACCAAAAA ATTCAAAAAT TTAATGTGAT      960

TTGGTCAATC GATCTACGTC CATAAAGGAG ATGAGTAATC TACTATAAAT ATGAGAGTAC     1020

AAAATACAGA GAGAAACAAC CTCAACTAAT TCACTCGGAA TACATGAGAA GTTCACACAA     1080

GTGATAACGT ATCAAACTTG TGACCCACAC TTTTCCCTCT AACCAAAGCT CTTAAAACTA     1140

TATTGTGAAT GCTGATTAAG TTAAACGAAA CAGTCCTAAA TCTTTTCCGT CCTATGAGAA     1200

ACAAGATTAA TCAATTCACA ATTTTTTTAA AAAGAAAAAC CTGTAAGAAA TTTAGGCAAA     1260

CAAAACCTAA CACAAGTTTG TTTTTGTTTT TACTACCAAC AAGAAATTCA AATGGCAAAT     1320

GTATAACGCA TCTTAGCTAA TTATATGACC AGATTCAGAT TAATATACAT CTTCACCCAT     1380

GCAATCCATT TCTATATAAA GAAACATACA CGAACTTGAT ATTATTAGAG ATTGAGCA      1438

ATG GAG GGT AAC AAC AGC AGT AGC AAG TCA ACC ACC AAT CCA GCA TTG      1486
Met Glu Gly Asn Asn Ser Ser Ser Lys Ser Thr Thr Asn Pro Ala Leu
 1               5                  10                  15

GAT CCG GAT CTG GAC AGC CCG GAT CAG CCG GGT CTG GAG TTT GCC CAA      1534
Asp Pro Asp Leu Asp Ser Pro Asp Gln Pro Gly Leu Glu Phe Ala Gln
             20                  25                  30

TTT GCT GCC GGC TGC TTT TGG GGA GTC GAA TTG GCT TTC CAG AGG GTT      1582
Phe Ala Ala Gly Cys Phe Trp Gly Val Glu Leu Ala Phe Gln Arg Val
         35                  40                  45

GGA GGA GTA GTG AAG ACG GAG GTT GGG TAC TCT CAG GGG AAT GTC CAT      1630
Gly Gly Val Val Lys Thr Glu Val Gly Tyr Ser Gln Gly Asn Val His
     50                  55                  60

GAC CCG AAC TAC AAG CTT ATT TGC TCC GGA ACA ACC GAA CAT GCC GAG      1678
Asp Pro Asn Tyr Lys Leu Ile Cys Ser Gly Thr Thr Glu His Ala Glu
 65                  70                  75                  80

GCC ATT CGG ATC CAG TTT GAC CCG AAT GTC TGC CCG TAT TCC AAT CTC      1726
Ala Ile Arg Ile Gln Phe Asp Pro Asn Val Cys Pro Tyr Ser Asn Leu
                 85                  90                  95

CTT TCT CTA TTT TGG AGT CGC CAT GAC CCG ACC ACT CTA AAT CGC CAG      1774
Leu Ser Leu Phe Trp Ser Arg His Asp Pro Thr Thr Leu Asn Arg Gln
            100                 105                 110

GTATCAAATT CCTTTGGTGT TCATTTTAT GTGATTAATA TTAAAAATTT TTTATATAAA     1834

TGTCATGATG ATGGTTGTTG CTAG GGT AAT GAT GTG GGA AAG CAA TAC CGC       1885
              Gly Asn Asp Val Gly Lys Gln Tyr Arg
                1               5

TCA GGA ATA TAT TAC TAT AAT GAT GCT CAG GCT CAA CTG GCA AGG GAG      1933
Ser Gly Ile Tyr Tyr Tyr Asn Asp Ala Gln Ala Gln Leu Ala Arg Glu
 10                  15                  20                  25

TCG TTA GAA GCT AAG CAG AAG GAA TTT ATG GAT AAG AAA ATT GTC ACT      1981
```

```
       Ser Leu Glu Ala Lys Gln Lys Glu Phe Met Asp Lys Lys Ile Val Thr
                    30                  35                  40

GAA ATT CTT CCT GCT AAG AGA TTT TAT AGA GCT GAA GAG TAT CAC CAG       2029
Glu Ile Leu Pro Ala Lys Arg Phe Tyr Arg Ala Glu Glu Tyr His Gln
                45                  50                  55

CAA TAT CTA GAG AAG GGT GGG GGC AGA GGT TGT AAG CAG TCG GCT GCA       2077
Gln Tyr Leu Glu Lys Gly Gly Gly Arg Gly Cys Lys Gln Ser Ala Ala
                60                  65                  70

AAG GGC TGC AAT GAC CCA ATA AGG TGC TAC GGT TGACAGCAGA TCTTTGAATG     2130
Lys Gly Cys Asn Asp Pro Ile Arg Cys Tyr Gly
                75                  80                  85

TCATAGCAAC TACAAAAGAA CTTGTTAGAC ATTTGCTGTC TTGCTTCTTT AAATTTGAAT    2190

AAACATGACA ATGATTCTTA TAACTACTTG CTCTCTTGGA TGGAATAACT AGTTGTCGTA    2250

AAGTATTCTC CTCTTGCTAA TTATTATCTC TCTTTATATG GTACCTGCAA TTTGTTGCTT    2310

TAGTTACAGA ATAATGGACG TCAATTCTAT ATCTTAATTT GTTTTAAGTC TTAAATGAGG    2370

TGGTTTGTGT TTGAAAGCAA TATCAAGCAT AGTAATACCA ATGATTTAGT AGATGAACTT    2430

AATCAAATCA AATTCCAAAA TGCAGTCTAC AAATTGACAA CATGAAGTTA AGTGTATCTT    2490

ATGTAAATTG ACATCTTTCC TAGTAGATGC CTAATACTTT TGTAAAGACT AAAATAAGCA    2550

CAGATGAGGC TTGTGCATTT AACTTAGAGT TCATCCTTAG GTGTGGCTGC AGGAGACCCT    2610

GTAGGGTTGC TTGAAGTCTT GATGGGGTAG GAGGGTTGCA TTGCTATACC ACACAACCCC    2670

TCTTCAGCGT CAACCTTGCG CTGCATTCTA ATGTATCCTT TTTCTCCCCA TTCAGCTCCC    2730

CATGAGTTCT TCACAATCCA GTATTTGGTT CCATCGACGG TTGTGCCATA CCCCACAATA    2790

GCCACA                                                               2796

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: 5' PCR primer sequence, E4G5 #72,
            corresponding to the region between nucleotides 1439 and
            1452 of the tomato E4 gene (xi) SEQUENCE DESCRIPTION: SEQ ID NO:6:

AGC CAT GGA GGG TAA CAA                                              18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PCR 3'primer, E4G3 #73, corresponding
``` to the region between nucleotides 2160 and 2177 of the E4
gene (xi) SEQUENCE DESCRIPTION: SEQ ID NO:7:

GAA GCA AGA CAG CAA ATG                                             18

(2) INFORMATION FOR SEQ ID NO:8:

(i) SEQUENCE CHARACTERISTICS:
        (A) LENGTH: 191 amino acids
        (B) TYPE: amino acid
        (C) STRANDEDNESS: double
        (D) TOPOLOGY: linear (ii) MOLECULE TYPE: protein (iii) HYPOTHETICAL: NO (iv) ANTI-SENSE: NO (vi) ORIGINAL SOURCE:
         (C) INDIVIDUAL ISOLATE: RASPBERRY E4 PROTEIN (xi) SEQUENCE DESCRIPTION: SEQ ID NO:8:

Met Ala Ser Thr Thr Thr Asn Asn Pro Ala Leu Asp Pro Asp Ser Asp
1               5                   10                  15

Thr Pro Asp Asn Pro Gly His Glu Phe Ala Gln Phe Gly Ser Gly Cys
            20                  25                  30

Phe Trp Gly Ala Glu Leu Arg Phe Gln Arg Val Ala Gly Val Val Lys
        35                  40                  45

Thr Glu Val Gly Tyr Ser Gln Gly His Val His Asp Pro Asn Tyr Lys
    50                  55                  60

Leu Val Cys Ser Gly Thr Thr Asn His Ser Glu Val Val Arg Val Gln
65                  70                  75                  80

Phe Asp Pro Gln Val Tyr Pro Tyr Ser Asp Leu Leu Ser Val Phe Trp
                85                  90                  95

Ser Arg His Asp Pro Thr Thr Val Asn Arg Gln Gly Gly Asp Val Gly
            100                 105                 110

Thr Gln Tyr Arg Ser Gly Ile Tyr Tyr Tyr Asn Glu Thr Gln Ala Arg
        115                 120                 125

Leu Ala Gln Glu Ser Lys Glu Ala Lys Gln Leu Glu Phe Lys Asp Lys
    130                 135                 140

Lys Val Val Thr Glu Ile Leu Pro Ala Lys Arg Phe Tyr Arg Ala Glu
145                 150                 155                 160

Glu Tyr His Gln Gln Tyr Leu Ala Lys Gly Gly Gly Asn Gly Asn Lys
                165                 170                 175

Gln Ser Ala Glu Lys Gly Cys Asn Asp Pro Ile Arg Cys Tyr Gly
            180                 185                 190

(2) INFORMATION FOR SEQ ID NO:9:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: raspberry E4 gene DNA fragment (ix) FEATURE:
    (A) NAME/KEY: CDS
    (B) LOCATION: 1..213

(xi) SEQUENCE DESCRIPTION: SEQ ID NO:9:

| | | | | | | | | | | | | | | | |
|---|---|---|---|---|---|---|---|---|---|---|---|---|---|---|---|
| GAG | CTC | AGG | TTT | CAG | CGA | GTG | GCC | GGT | GTG | GTC | AAG | ACC | GAG | GTT | GGG | 48 |
| Glu | Leu | Arg | Phe | Gln | Arg | Val | Ala | Gly | Val | Val | Lys | Thr | Glu | Val | Gly |
| 1 | | | | 5 | | | | | 10 | | | | | 15 |

| TAC | TCC | CAG | GGC | CAC | GTC | CAC | GAT | CCG | AAT | TAC | AAA | CTG | GTC | TGC | TCC | 96 |
|---|---|---|---|---|---|---|---|---|---|---|---|---|---|---|---|---|
| Tyr | Ser | Gln | Gly | His | Val | His | Asp | Pro | Asn | Tyr | Lys | Leu | Val | Cys | Ser |
| | | | 20 | | | | | 25 | | | | | 30 | | |

| GGA | ACT | ACC | AAC | CAT | TCG | GAG | GTC | GTT | CGG | GTC | CAG | TTC | GAC | CCG | CAA | 144 |
|---|---|---|---|---|---|---|---|---|---|---|---|---|---|---|---|---|
| Gly | Thr | Thr | Asn | His | Ser | Glu | Val | Val | Arg | Val | Gln | Phe | Asp | Pro | Gln |
| | | 35 | | | | | 40 | | | | | 45 | | | |

| GTC | TAC | CCA | TAC | TCG | GAC | CTG | CTT | TCC | GTC | TTT | TGG | TCT | CGT | CAT | GAT | 192 |
|---|---|---|---|---|---|---|---|---|---|---|---|---|---|---|---|---|
| Val | Tyr | Pro | Tyr | Ser | Asp | Leu | Leu | Ser | Val | Phe | Trp | Ser | Arg | His | Asp |
| | 50 | | | | | 55 | | | | | 60 | | | | |

| CCA | ACG | ACT | GTC | AAT | CGC | CAG | GTATGGGGAT | TG | | | | | | | | 225 |
|---|---|---|---|---|---|---|---|---|---|---|---|---|---|---|---|---|
| Pro | Thr | Thr | Val | Asn | Arg | Gln |
| 65 | | | | | 70 | |

It is claimed:

1. A chimeric gene, comprising a promoter which in its native form is associated with a nucleotide coding sequence, wherein said nucleotide coding sequence will hybridize to the nucleotide coding sequence of the raspberry E4 gene presented as SEQ ID NO:2, wherein hybridization is conducted at 42° C. in 50% formamide, 5×SSC, 5×Denhardt's solution, 0.5% SDS and 100 µg/ml denatured carrier DNA, followed by washing two times in 2×SSC and 0.5% SDS at room temperature and two additional times in 0.1×SSC and 0.5% SDS at 42° C., and said promoter is operably linked to a heterologous nucleotide sequence encoding a product of interest and thereby effects constitutive expression of said product of interest.

2. The chimeric gene of claim 1, wherein the nucleotide sequence of said promoter corresponds to the sequence presented as SEQ ID NO:1.

3. A method for producing a transgenic plant, comprising:
   introducing into progenitor cells of the plant a chimeric gene according to claim 1, and growing the transformed progenitor cells to produce a transgenic plant.

4. A method for providing expression of a selectable marker gene in transgenic plants, comprising:
   (i) introducing into progenitor cells of a plant the chimeric gene of claim 1,
   wherein said nucleotide, coding sequence comprises a selectable marker gene functional in plant cells, and expression of said selectable marker gene confers to plant cells in which said gene is expressed the ability to grow in the presence of a selective agent,
   (ii) selecting plant cells which have been transformed by their ability to grow in the presence of an amount of said selective agent that is toxic to non-transformed plant cells,
   (iii) regenerating said transformed plant cells to provide a differentiated plant, and
   (iv) selecting a transformed plant which expresses said selectable marker.

5. The method of claim 4, where said introducing includes transforming progenitor cells of the plant with a vector containing said chimeric gene.

6. The method of claim 4, where said selective agent is selected from the group consisting of hygromycin, geneticin, and kanamycin.

7. The method of claim 4, where said selectable marker gene is selected from the group consisting of a neomycin phosphotransferase (npt) gene, a hygromycin phosphotransferase (hpt) gene, and a bromoxynil-specific nitrilase (bxn) gene.

8. A kit comprising the chimeric gene of claim 1.

9. The chimeric gene according to claim 1, wherein said nucleotide coding sequence encodes a polypeptide that permits selection of transformed plant cells containing said gene by rendering said cells resistant to an amount of an antibiotic that would be toxic to non-transforted plant cells.

10. The chimeric gene according to claim 9, wherein said product of interest is selected from the group consisting of neomycin phosphotransferase, hygromycin phosphotransferase and bromoxynil-specific nitrilase.

11. The chimeric gene according to claim 1, wherein said heterologous nucleotide sequence encodes a polypeptide which confers herbicide-resistance to transformed plant cells expressing said polypeptide.

12. The chimeric gene according to claim 1, wherein said heterologous nucleotide sequence comprises nptII gene.

13. An isolated DNA molecule comprising a constitutive promoter which in its native form is associated with a nucleotide coding sequence, wherein said nucleotide coding sequence will hybridize to the nucleotide coding sequence of the raspberry E4 gene presented as SEQ ID NO:2, wherein hybridization is conducted at 42° C. in 50% formamide, 5×SSC, 5×Denhardt's solution, 0.5% SDS and 100 µ/ml denatured carrier DNA, followed by washing two times in 2×SSC and 0.5% SDS at room temperature and two additional times in 0.1×SSC and 0.5% SDS at 42° C.

14. The isolated DNA molecule according to claim 13, wherein the nucleotide sequence of said promoter is contained in the sequence presented as SEQ ID NO:2.

15. The isolated DNA molecule according to claim 13, wherein the nucleotide sequence of said promoter corresponds to the sequence presented as SEQ ID NO:1.

16. A plant cell comprising: a chimeric gene comprising a promoter which in its native form is associated with a nucleotide coding sequence, wherein said nucleotide coding sequence will hybridize to the nucleotide coding sequence of the raspberry E4 gene presented as SEQ ID NO:2, when hybridization is conducted at 42° C. in 50% formamide, 5×SSC, 5×Denhardt's solution, 0.5% SDS and 100 μg/ml denatured carrier DNA, followed by washing two times in 2×SSC and 0.5% SDS at room temperature and two additional times in 0.1×SSC and 0.5% SDS at 42° C., wherein said promoter is operably linked to a heterologoua nucleotide sequence encoding a product of interest and thereby effects constitutive expression of said heterologous nucleotide sequence in said plant cell.

17. A plant cell comprising the chimeric gene of claim 2.
18. A plant cell comprising the chimeric gene of claim 9.
19. A plant cell comprising the chimeric gene of claim 11.
20. A plant cell comprising the chimeric gene of claim 12.

21. A transgenic plant comprising a chimeric gene comprising a a promoter which in its native form is associated with a nucleotide coding sequence, wherein said nucleotide coding sequence will hybridize to the nucleotide coding sequence of the raspberry E4 gene presented as SEQ ID NO:2 when hybridization is conducted at 42° C. in 50% formamide, 5×SSC, 5×Denhardt's solution, 0.5% SDS and 100 μg/ml denatured carrier DNA, followed by washing two times in 2×SSC and 0.5% SDS at room temperature and two additional times in 0.1×SSC and 0.5% SDS at 42° C., wherein said promoter is operably linked to a heterologous nucleotide sequence encoding a product of interest and thereby effects constitutive expression of said heteroloqous nucleotide sequence in said plant.

* * * * *